United States Patent
Tseng et al.

(10) Patent No.: US 11,253,191 B2
(45) Date of Patent: Feb. 22, 2022

(54) SKIN DETECTION DEVICE

(71) Applicant: Li-Tek Technology Co., Ltd., Zhunan Township, Miaoli County (TW)

(72) Inventors: Chih-Ming Tseng, Zhunan Township, Miaoli County (TW); Tai-Wei Su, Tainan (TW)

(73) Assignee: LI-TEK TECHNOLOGY CO., LTD., Zhunan Town, Miaoli County (TW)

( * ) Notice: Subject to any disclaimer, the term of this patent is extended or adjusted under 35 U.S.C. 154(b) by 625 days.

(21) Appl. No.: 15/822,885

(22) Filed: Nov. 27, 2017

(65) Prior Publication Data

US 2018/0310872 A1    Nov. 1, 2018

(30) Foreign Application Priority Data

Apr. 27, 2017 (TW) .................................. 106114089

(51) Int. Cl.
| | |
|---|---|
| *A61B 5/00* | (2006.01) |
| *A61B 5/1455* | (2006.01) |
| *G02B 27/28* | (2006.01) |
| *G02B 19/00* | (2006.01) |
| *A61B 5/103* | (2006.01) |
| *G02B 5/30* | (2006.01) |
| *A61B 5/0531* | (2021.01) |

(52) U.S. Cl.
CPC ............ *A61B 5/443* (2013.01); *A61B 5/0013* (2013.01); *A61B 5/0077* (2013.01); *A61B 5/14558* (2013.01); *A61B 5/0531* (2013.01); *A61B 5/1032* (2013.01); *A61B 2576/00* (2013.01); *G02B 5/30* (2013.01); *G02B 19/0095* (2013.01); *G02B 27/286* (2013.01)

(58) Field of Classification Search
None
See application file for complete search history.

(56) References Cited

U.S. PATENT DOCUMENTS

| 6,105,869 A | * | 8/2000 | Scharf | G06K 7/10742 |
| | | | | 235/454 |
| 2004/0174525 A1 | * | 9/2004 | Mullani | G01N 21/6445 |
| | | | | 356/369 |
| 2005/0197582 A1 | * | 9/2005 | Ferguson | A61B 5/0059 |
| | | | | 600/476 |
| 2006/0161226 A1 | * | 7/2006 | McMickle | A61N 5/0617 |
| | | | | 607/88 |
| 2007/0040907 A1 | * | 2/2007 | Kern | A61B 5/0059 |
| | | | | 348/77 |

(Continued)

FOREIGN PATENT DOCUMENTS

CN    106333644 A  *  1/2017

*Primary Examiner* — Pascal M Bui Pho
*Assistant Examiner* — Farouk A Bruce
(74) *Attorney, Agent, or Firm* — Muncy, Geissler, Olds & Lowe, P.C.

(57) ABSTRACT

The invention provides a skin detection device using different detecting lights, such as white light or UV light. When white light is used, the user's original skin image is acquired, and further analyzed to determine the user's skin condition, such as pore size or dullness of spots. When UV light is used, it is determined whether there is metal remnant or acne on the user's skin. By using the skin detection device, various user skin conditions can be found to help the following cosmetic consultation.

7 Claims, 18 Drawing Sheets

(56) References Cited

U.S. PATENT DOCUMENTS

| | | | |
|---|---|---|---|
| 2010/0076272 A1* | 3/2010 | Moromizato | A61B 5/489 600/249 |
| 2013/0148326 A1* | 6/2013 | Goldfain | G01N 21/4795 362/19 |
| 2014/0300721 A1* | 10/2014 | Imamura | H04N 9/643 348/77 |
| 2016/0331314 A1* | 11/2016 | Bhansali | A61B 5/0261 |
| 2018/0218496 A1* | 8/2018 | Sinai | A61B 5/0077 |

* cited by examiner an application program installed in the receiving device performs the comparison of the user skin oil and water analyzed frequency, and thus the water content and the oil content of user skin is obtained correspondingly, and the oil and water content of user skin is further used to analyze the softness of the user skin — S45 the receiving device presents the previously described analysis results on the oil and water content of user skin and the softness of user skin to the user and operator — S46

Fig. 5C

SKIN DETECTION DEVICE

CROSS-REFERENCE TO RELATED APPLICATIONS

This application claims priority to Taiwan Patent Application No. 106114089, filed Apr. 27, 2017, the content of which are hereby incorporated by reference in their entirety.

FIELD OF THE INVENTION

The present invention provides a skin detection device, particularly related to a skin detection device. The skin detection device is used to detect a user's skin condition including spot, pore, wrinkle, texture, and roughness or softness of the skin, the metal content on the skin surface and oil and water content of the user's skin.

BACKGROUND OF THE INVENTION

Even though there is an economic slump, the market of aesthetic medicine still grows steadily, especially the market related to the skin tone of the face, which reveals that people always seek beauty inherently. Therefore, developing apparatuses to be used in aesthetic medicine has promising potential of growth.

The skin detection apparatuses currently used in cosmetic dermatology on the market present were applying more than one lens but lack of lightness management in a detecting light so that a skin image formed by a reflective light reflected from the skin brought about poor resolution, such as the pore size, roughness, or moisture content of skin, even if polarization theory of the specular and diffused reflections was widely used that was disclosed by the conventional prior art as US Publication No. 20130148326. The conventional prior art as China Published Patent CN106333644A disclosing skin photographing detecting technology which detects only one skin condition such as a user skin oil and water content. Therefore, when various skin conditions are required to be shown, people have to use multiple kinds of detecting apparatus, which results in the inconvenience of aesthetic consulting.

Based on the aforementioned problems, a skin detection apparatus having improved resolution on reflective skin images is demanded in aesthetic industry to acquire various information of a user's skin conditions, such as the roughness or softness of the skin, or the metal content on the skin surface, so that the operating problems of the operator can be relieved, and thereby it improves the efficiency of aesthetic consulting.

SUMMARY OF THE INVENTION

To solve the aforementioned drawbacks, a primary objective of the present invention is to provide a skin detection device. The skin detection device is devised with one polarizer or multiple polarizers disposed appropriately to improve the resolution of reflective images of skin, thereby, the conditions of various users, such as spots or wrinkles and pore sizes, can be found.

It is an objective of the present invention is to provide a skin detection device. The skin detection device is devised with UV LED (Ultraviolet light-emitting diode) bulbs to determine whether there is remnant metal of the cosmetics and to ascertain whether there is breeding of germs or piling up of keratin on the user's skin.

It is another objective of the present invention is to provide a skin detection device. The skin detection device is devised with an oil and water detecting component to determine the user skin oil and water analyzed frequency for obtaining the water content and oil content, and to further estimate the softness of the user's skin.

According to the aforesaid objectives, the present invention firstly provides a skin detection device including the constituent elements as below. A LED light board equipped with a plurality of white light LED bulbs and a plurality of UV LED bulbs, for providing the skin detection device with detecting light required for operation. A first polarizer configured on the LED light board for filtering a reflective light reflected from the detecting light casting onto the face of a user, to obtain a polarized light signal. A lens module with one end connected to an end of the LED light board, wherein the lens module is used for receiving the aforesaid polarized light signal and then transmitting an electrical signal to a circuit mainboard. A circuit mainboard with one end connected to an end of the lens module, wherein the circuit mainboard is configured with a light source control switch, a photography control switch, a power switch, a wireless transmission module, and a signal processing module. The circuit mainboard is used for receiving the electrical signal and then processing the electrical signal into user original skin image, and further transmitting this user original skin image to the wireless transmission module. The wireless transmission module then transmits the user original skin image to the receiving device. The light source control switch allows the white light LED bulbs and the UV LED bulbs are switched according to the requirements; the photography control switch controls the lens module to capture images and the operator can therefore acquire the user original skin image. A charging board with one end connected to the other end of the circuit mainboard, wherein the charging board is used for charging. A lithium battery, which is disposed on the circuit mainboard and provides the power needed for operating this skin detection device. A lower cover having an accommodating space, wherein the accommodating space contains the LED light board, the lens module, the circuit mainboard, the charging board, and the lithium battery. An upper cover connected with the lower cover, wherein the upper cover is further devised with an upper cover ornamental ring and a plurality of buttons. These buttons are connected with the light source control switch, the photography control switch, and the power switch, in order to assist the operator to choose the expected detecting light and to switch on the camera module for acquiring the user original skin image and for assisting the operator to start the skin detection device. And a LED lampshade, wherein the LED lampshade is configured near the front ends of the upper cover and the lower cover for supporting the connection between the upper cover and the lower cover.

According to the aforesaid objectives, the present invention further includes an oil and water detecting portion. One end of the oil and water detecting portion is connected to the aforesaid LED lampshade. This oil and water detecting portion includes the oil and water detecting probe, head cover, head cover ornamental ring and dust cover. The dust cover is disposed on the head cover, wherein the oil and water detecting probe is used to obtain the user skin oil and water analyzed frequency, and then the wireless transmission module transmits this user skin oil and water analyzed frequency to the receiving device.

The skin detection device herein further includes a tail cover portion. The tail cover portion is configured near the rear ends of the upper cover and the lower cover. The tail cover portion includes a tail cover ornamental ring, a tail cover and a tail cover soft plug. The tail cover soft plug is configured on the tail cover; and one end of the tail cover is connected the tail cover ornamental ring. This tail cover portion is designed for securing the skin detection device while operating.

Because the skin detection device has a plurality of white light LED bulbs and a plurality of UV LED bulbs, when the operator uses this skin detection device and chooses the white light as the detecting light, the skin detection device obtains the user original skin image related to the user's skin condition. On the other hand, when the operator chooses UV light as the detecting light, the skin detection device determines whether there are metal remnants, clogged pores, piling up of keratin presented on user's skin. The skin detection device further includes the oil and water detecting portion to obtain the user skin oil and water analyzed frequency, and the aforesaid user skin oil and water analyzed frequency can be transmitted to the receiving device by the wireless transmission module devised in this skin detection device. The receiving device is installed an application program to analyze and compare the aforementioned user original skin image and user skin oil and water analyzed frequency respectively, and the application program ultimately presents the analysis index and the oil and water content concerning the user's skin condition to the user and operator. In this way, various data of user's skin condition are acquired for the subsequent aesthetic advice.

According to the aforementioned objects, the invention herein provides a method of detecting a user's skin condition by utilizing the aforesaid skin detection device, which includes the following steps:

The operator starts the skin detection device, and switch on the white light LED bulb; the operator checks the interconnection between the skin detection device and the receiving device; the operator aims the opening of the skin detection device toward the user's skin to execute the skin detection; and the operator chooses whether to perform the analysis of user's skin condition. The user can use this method to understand his/her skin condition such as pore size, the dullness of spots or the severity of wrinkles to gain the aesthetical advices.

In order to enable the users to obtain the analysis index related to their skin condition by using the skin detection device according to the present invention, and thus let the user and the operator find out the user's skin condition, a user skin condition analysis process is further provided herein. After the aforesaid user original skin image is transmitted to the receiving device, the application program installed in the receiving device is therefore started, and then this analysis process is performed by the application program. This analysis process includes the steps below:

The application program preprocesses the user original skin image acquired by the skin detection device, and generates the user skin image. This user skin image is obtained firstly by executing the photographing function of the lens module devised in the detection device, and then by processing the signals via the signal processing module. The application program performs a color contrast enhancement on the user skin image and obtains a contrast-enhanced user skin image. The application program sorts the contrast-enhanced user skin image according to the purposes of analysis via utilizing the graphics application program installed in a mobile device to sorts the contrast-enhanced skin image by skin defects and skin textures. And the application program executes a post process on the contrast-enhanced user skin image to obtain an analyzed result, and then presents this analyzed result as an analysis index to the user, where in the post process includes image edge detection and an image color stratification analysis. By performing the aforesaid analysis process, the receiving device herein can present the analysis index concerning the user's skin condition to the user and the operator, therefore they obtains various information related to user skin condition, such as the dullness of spots, the pore sizes or the severity of wrinkles.

An analysis process of skin oil and water content is further provided herein and it allows the skin detection device according to the present invention to provide the user with the oil and water content of skin. The oil and water detecting probe obtains the user skin oil and water resistance signal, and then the circuit mainboard processes this user skin oil and water resistance signal into a user skin oil and water resistance signal, which is transmitted to a receiving unit for performing the following analysis process, comprising the steps listed below:

An application program installed in the receiving unit compares the oil and water analyzed frequency to obtain the water content of skin, the oil content of skin, and the softness of skin; and the receiving device presents the result of aforementioned comparison to the user and operator.

According to the aforesaid analysis process, the user and operator herein obtain multiple skin detection results include the water content of skin, the oil content of skin and the softness of skin.

Due to the skin detection device provided in the present invention is devised simultaneously with white light LED bulbs and oil and a water detecting probe, this device is able to obtain various data at the same time, such as the user original skin image or the user skin oil and water analyzed frequency; and the present invention further provides the analysis process required by those aforesaid data, it allows the skin detection device to obtain various information related to user's skin condition, such as pore size, dullness of spots, piling up of keratin, skin textures, skin roughness, severity of wrinkles, moisture content, oil content and softness. Furthermore, this skin detection device is further devised with UV LED bulbs, so that it can detect and immediately find out if there are metal remnants, clogged pores, piling up of keratin presented on user's skin. The relevant personnel such as beauticians can provide the user with aesthetic advices according to the information obtained as previously described, and therefore improving the efficiency of aesthetic consulting.

BRIEF DESCRIPTION OF THE DRAWINGS

FIG. 5C is a flow chart showing the analysis process of a skin oil and water content in accordance with the present invention.

DETAILED DESCRIPTION OF THE INVENTION

Figure 1A:
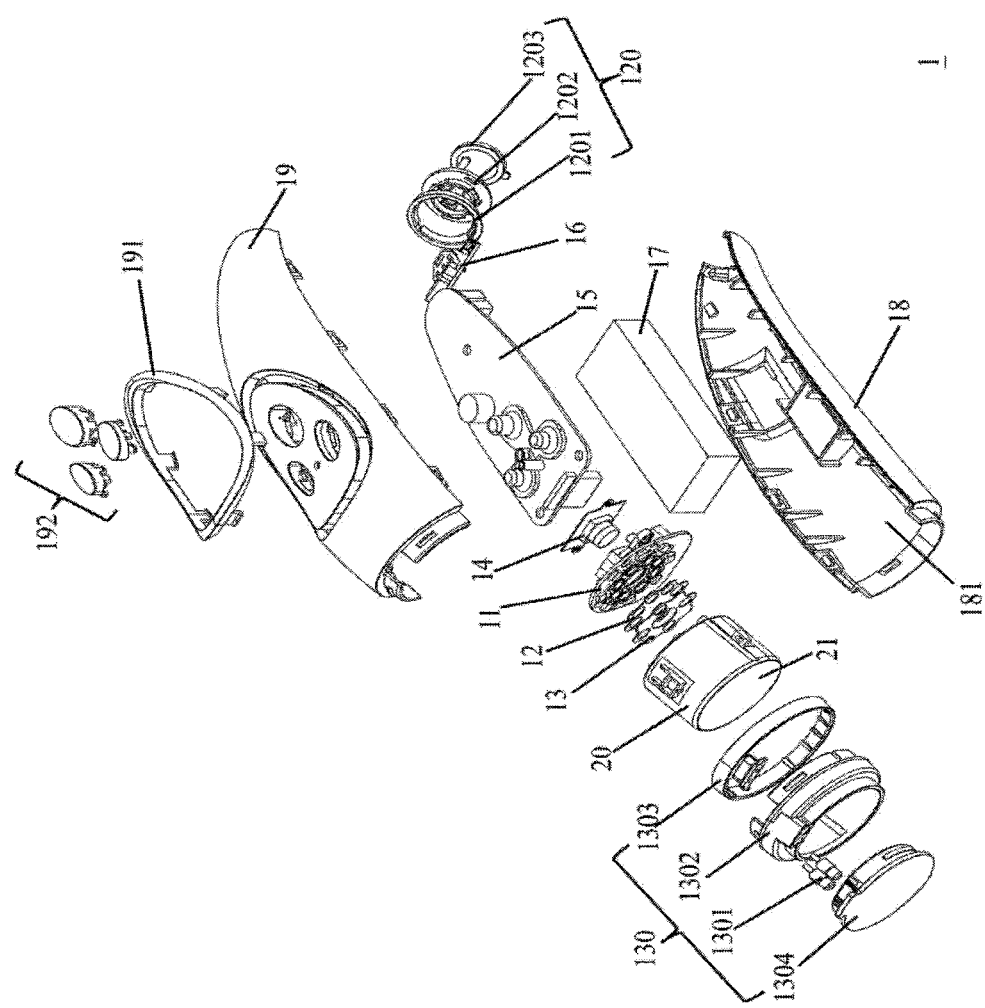
FIG. 1A is an exploded view of the overall structure of the skin detection device in accordance with the present invention.

For those skilled in the art to better understand the technical details of the skin detection device according to the present invention, relevant embodiments and examples are described hereinafter. The fundamental principles involved in optics, electricity, communications, and image processing are not described additionally in the following description. Nevertheless, an interpretation of this invention needs to be addressed beforehand: regarding the inventive features and their embodiments of the skin detection device according to the present invention, for example, each of the constituent elements are connected by metal wires to enable the structural connections to one another. Moreover, please refer to the drawings and the detailed description below while reading the descriptions according to the present invention, wherein the shape and relative size of each constituent element showed in the drawing are used accessorily for illustrating the details of the description, and they are not intended to be used for limiting the shape and relative size of each constituent element, which needs to be addressed beforehand.

Figure 1B:
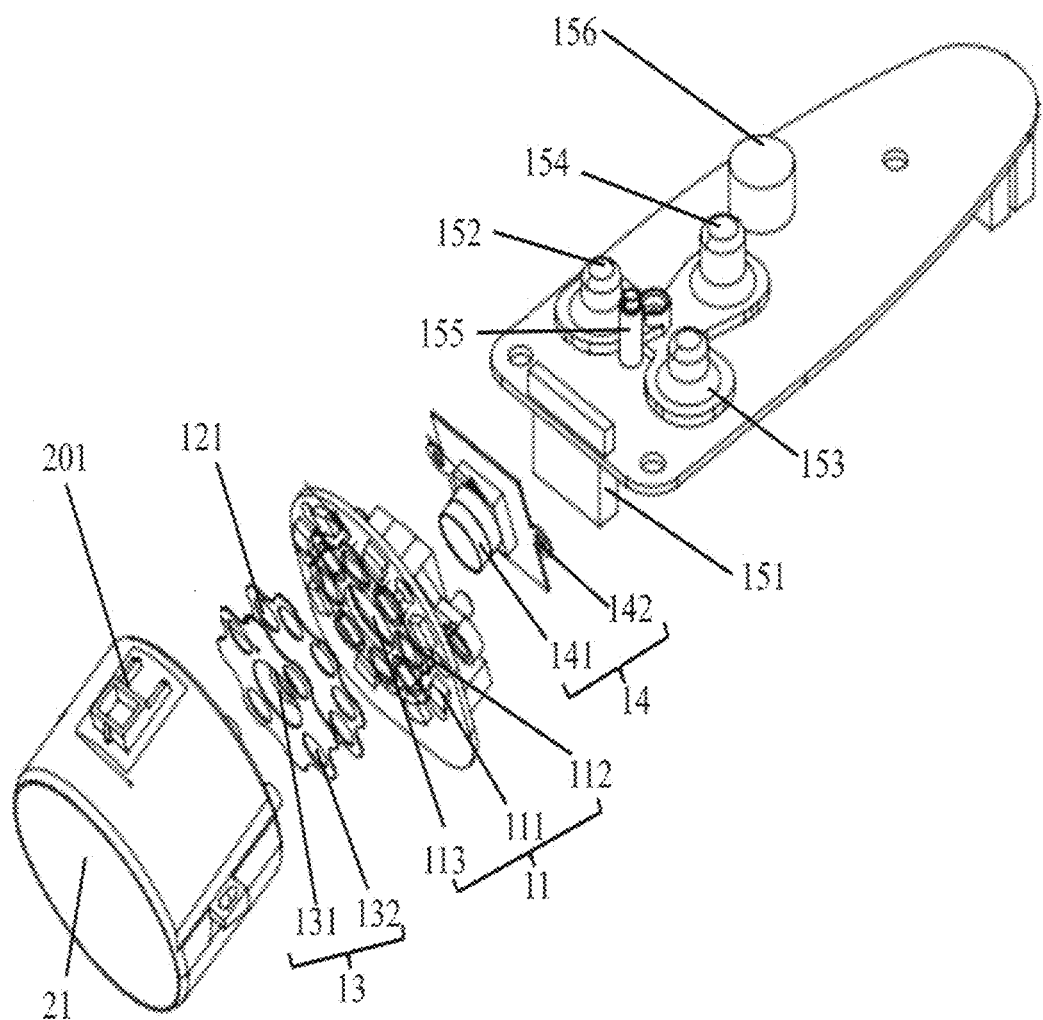
FIG. 1B is a locally enlarged exploded view of the skin detection device in accordance with the present invention.
Figure 2A:
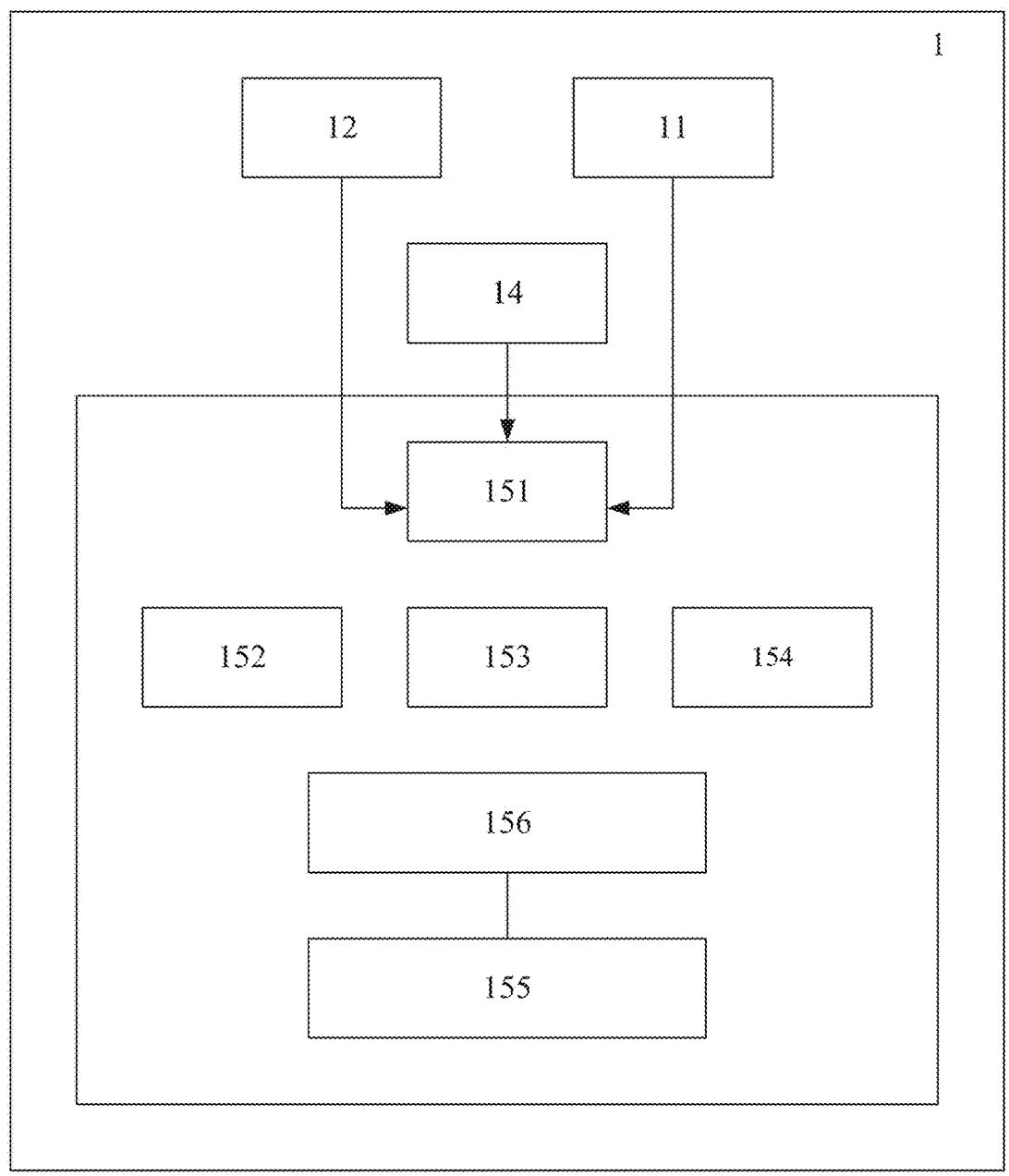
FIG. 2A is a block diagram schematically demonstrating the skin detection device in accordance with the present invention.

Please refer to FIG. 1A, FIG. 1B and FIG. 2A, in which FIG. 1A is an exploded view of the overall structure of the skin detection device in accordance with the present invention; FIG. 1B is a locally enlarged exploded view of the skin detection device in accordance with the present invention; and FIG. 2A is a block diagram schematically demonstrating the skin detection device in accordance with the present invention. First, as shown in FIG. 1A, the skin detection device 1 includes the following constituent components: a LED light board 11, the LED light board 11 is configured a plurality of white light LED bulbs 111 and a plurality of UV LED bulbs 112, and a hollow area 113 is configured in the middle of the LED light board 11, wherein the white light LED bulbs 111 and the UV LED bulbs 112 are used herein for providing the detecting light required for operating the skin detection device 1. In one embodiment, eight white light LED bulbs 111 and eight UV LED bulbs 112 are respectively allocated. Besides, the white light LED bulbs 111 and the UV LED bulbs 112 are designed to encircle the hollow area 113 to form concentric circles, wherein the white light LED bulbs 111 are allocated around the periphery of the concentric circles; and the UV LED bulbs 112 are allocated near the intermediate circle of the concentric circles. Based on the aforementioned disposition, the purpose of allocating the white light LED bulbs 111 around the periphery of the concentric circles is to obtain the user original skin image of a user; and the purpose of allocating the UV LED bulbs 112 near the intermediate circle of the concentric circles is to detect whether there are metal remnants, clogged pores, piling up of keratin presented on the user's skin. For example, if there are metal remnants, there will be fluorescence on the user's skin, indicating that the cosmetics used by the user may contains metal ingredients; if there are red speckles on the skin, it indicates that the pores are clogged by growing germs; and if the there are white speckles on the skin, it indicates that the pores are clogged by piling of keratin.

Next, please continue to refer to FIG. 1A. The first polarizer 12 is a flat plate, and a plurality of holes 121 are provided near the rim of the first polarizer 12, and the plurality of holes 121 are in accordance with the plurality of white light LED bulbs 111, in which the number of the holes 121 disposed in the first polarizer 12 can be adjust according to the number of white light LED bulbs 111, and it is not limited in this embodiment. Apparently, the major purpose of disposing these holes 121 in the first polarizer 12 is to allow the detecting light generated by the white light LED bulbs 111 to pass through the multiple holes 121 in the first polarizer 12 and to cast onto the face of a user. When the detecting light generated by the white light LED bulbs 111 is casted on the user's face skin, the light source will be scattered because the user's face skin is not a flat surface or because there is oil or water on the skin surface. Hence, when the scattering light reflected form the skin passes through the first polarizer 12, the first polarizer 12 filters the reflected scattering light to acquire polarized light signal, and thus the resolution of skin images is improved. Apparently, the constituent materials of the first polarizer 12 according to the present invention are not limited herein, materials having directional properties, such as poly vinyl alcohol (PVA), are suitable to be used.

Additionally, in order to provide better resolution on skin, the number of disposed polarizer can be adjusted according to the present invention. In one preferred embodiment of the present invention, for further controlling or tuning the brightness of the detecting light generated by the white light LED bulbs 111, a second polarizer 13 is further disposed near the lateral side of the first polarizer 12 facing the skin, as shown in FIG. 1B. A hole 131 is configured in the center of the second polarizer 13 corresponding to the hollow area 113 of the LED light board 11, and a plurality of holes 132 are allocated between the hole 131 and the rim of the second polarizer 13, wherein the number of the holes 132 are corresponding to the number of white light LED bulbs 111. The number of those holes 132 is adjustable for shading the detecting light generated by the white light LED bulbs 111 and thereby regulating the brightness of formed image, to finally accomplish the goal of improving the resolution. In one preferable embodiment, four holes 132 are allocated, and it consequently reduces the brightness of detecting light. Therefore, the detecting light generated from four of the eight white light LED bulbs 111 passes through the holes 132 and then casts onto the skin. The detecting light generated from other four white light LED bulbs 111 passes essentially through the second polarizer 13 to cast onto the skin; and then, the detecting light generated from other four white light LED bulbs 111 passes through the second polarizer 13, casts onto the skin, and is reflected. Most of the reflective light passes through the hole 132 of the second polarizer 13, and then passes through the first polarizer 12 to filter the scattering light, and finally forms the image in a lens module 14. Apparently, by disposing this second polarizer 13, the aim of controlling the brightness of the detecting light emitted from the white light LED bulbs 111 is achieved. The newly added second polarizer 13 can be allocated near a lateral end of the upper cover 19; and the constituent material of the second polarizer 13 herein is not limited as well. Materials having directional properties, such as poly vinyl alcohol (PVA), are suitable to be used.

And next, please continue to refer to FIG. 1A. The lens module 14 has one end connected to an end of the LED light board 11 for receiving the aforementioned polarized light signal. Furthermore, the lens module 14 is composed of a camera unit 141 and a soft board 142 (as shown in FIG. 1B); and the camera unit 141 penetrates the hollow area 113 of the LED light board 11, and thus one end of the lens module 14 is allowed to connect to one end of the LED light board 11, wherein the camera unit 141 can be a complementary metal oxide semiconductor (CMOS) image sensor. Additionally, the soft board 142 is connected to one end of the camera unit 141 for providing the power and the processing of the photoelectric conversion required by the camera unit 141. After the camera unit 141 of the lens module 14 receives polarized light signal, the camera unit 141 can convert the received polarized light signal into electrical signal by the CMOS devised inside the camera unit 141, and then transmit the electrical signal to the circuit mainboard 15 for processing the image signal.

Please further refer to FIG. 1A and FIG. 1B. A connector 151 is disposed at one end of the circuit mainboard 15. The connector 151 is configured to connect to the other end of the soft board 142 disposed on the lens module 14, and thus the two elements, the lens module 14 and the circuit mainboard 15, are mutually connected. Additionally, a first side of the circuit mainboard 15 is provided with a light source control switch 152, a photography control switch 153, a power switch 154, a wireless transmission module 155 and a signal processing module 156. Apparently, the light source control switch 152, the photography control switch 153, and the power switch 154 are connected to the circuit of the circuit mainboard 15, wherein the power switch 154 can connect to a lithium battery 17 provided on the other side of the circuit mainboard 15 by the connector 151. The light source control 152 is connected to the UV LED bulb 112, and the photography control switch 153 is connected to the lens module 14. On the other hand, the wireless transmission module 155 and the signal processing module 156 are configured in the circuit mainboard 15 and connect to each other.

Next, please continue to refer to FIG. 1A and FIG. 1B. A charging board 16 with one end connected to the lithium battery 17, and the charging board 16 herein can charge to store up the power in the lithium battery 17 for providing the power required by the skin detection device 1 during operation.

Please further refer to FIG. 1A and FIG. 1B. A lower cover 18 having an accommodating space 181 for containing the aforementioned LED light board 11, the lens module 14, the circuit mainboard 15, the charging board 16 and the lithium battery 17. An upper cover 19 used to connect or fasten the lower cover 18. An upper cover ornamental ring 191 and a plurality of buttons 192 are devised on the upper cover 19, wherein the plurality of buttons 192 are respectively connected or contacted to the light source control switch 152, the photography control switch 153, and the power switch 154. Thus the operator can start the skin detection device 1 to detect the user's skin; and the operator can choose the detecting light for various purposes, and acquire the user original skin image through switching on the lens module 14 by the photography control switch 153. And a LED lampshade 20 is configured near the front ends of the upper cover 19 and the lower cover 18 for supporting the connection between the upper cover 19 and the lower cover 18. Meanwhile, the connected LED lampshade 20 can form a circular opening 21, and this circular opening 21 can contact the skin of user. In a preferred embodiment, LED lampshade 20 is further disposed of a fixing unit (not shown) to ensure the LED lampshade 20, the lower cover 18 and the upper cover 19 are firmly connected.

Last, please continue to refer to FIG. 1A, the skin detection device is further devised with a tail cover portion 120. This tail cover portion 120 is configured near the rear ends of the upper cover 18 and the lower cover 17. The tail cover portion 120 comprises a tail cover ornamental ring 1201, a tail cover 1202 and a tail cover soft plug 1203; the tail cover soft plug 1203 is configured on the tail cover 1202; and one end of the tail cover 1202 is connected to the tail cover ornamental ring 1201. The tail cover portion 120 herein is designed for securing the connection between the upper cover 18 and the lower cover 17 of the skin detection device 1, and thus the skin detection device 1 is more firmly secured while operating.

Next, please refer to the FIG. 2A, which is a system block diagram demonstrating the skin detection device of the present invention. First, as shown in FIG. 2A, the skin detection device 1 is composed of a LED light board 11, a first polarizer 12, a lens module 14 and a circuit mainboard 15, wherein one end of the circuit mainboard 15 is provided with a connector 151 to connect to one end of the soft board 142 disposed on the lens module 14, and therefore the two elements, the lens module 14 and the circuit mainboard 15 are connected to each other. Additionally, the first side of the circuit mainboard 15 is further provided with a light source control switch 152, a photography control switch 153, a power switch 154, a wireless transmission module 155 and a signal processing module 156. Obviously, the light source control switch 152, the photography control switch 153, and the power switch 154 are connected to the circuit mainboard 15; and when the power switch 154 is turned on by the operator, the white light LED bulb 111 on the LED light board 11 and the lens module 14 are thus switched on. Therefore, when the operator covers the skin with the circular opening 21 of the LED lampshade 20 devised with the skin detection device 1, the white light LED bulb 111 can provide the light source for the lens module 14 to obtain the image of skin. The light source control switch 152 is connected to the UV LED bulb 112 for switching the white light LED bulb 111 to the UV LED bulb 112. For example, if the operator decides to check whether there is metal remnant or clogged pore on the user's skin, he/she can turn on the light source control switch 152, and at the same time, the circuit can switch to the UV LED bulb 112, and let the UV LED bulb 112 to shine the skin to determine whether there is metal remnant or clogged pore on the user's skin. The photography control switch 153 is connected to the power switch 154 for controlling the capture of current skin image observed via the skin detection device 1. If the operator decides to capture the image, he/she can press the photography control switch 153 and the skin detection device 1 subsequently completes the image capture of the skin area seen through the lens module 14. Additionally, because of that the wireless transmission module 155 devised on the circuit mainboard 15 and the signal processing module 156 are connected to each other, after the operator presses the photography control switch 153 and captures the image of the skin area seen through the lens module 14, the signal processing module 156 can convert the electrical signal from the lens module 14 into the user original skin image signal, and then, the user original skin image signal is further transmitted to the wireless transmission module 155 to further transmit this user original skin image signal to the receiving device 2. Finally, an application program installed in the receiving device 2 can process the aforesaid user original skin image signal.

Next, please continue to refer to FIG. 2A. According to the abovementioned description, in a preferable embodiment, the receiving device 2 can be a tablet or a smart phone, and the transmission of the abovementioned images can be done through a wireless communication, such as Bluetooth or WIFI technologies, wherein the light source control switch 152 allows the operator to switch between the white light LED bulb 111 and the UV LED bulb 112, and therefore the operator can use appropriate detecting light according to the purpose while the operator operates the skin detection device 1. The power switch 154 is herein used for controlling the start of the skin detection device 1. The photography control switch 153 is herein used for controlling the action of capturing image by the lens module 14, and thereby the operator can capture the image of the user's skin to obtain the user original skin image as previously described.

Figure 3A:
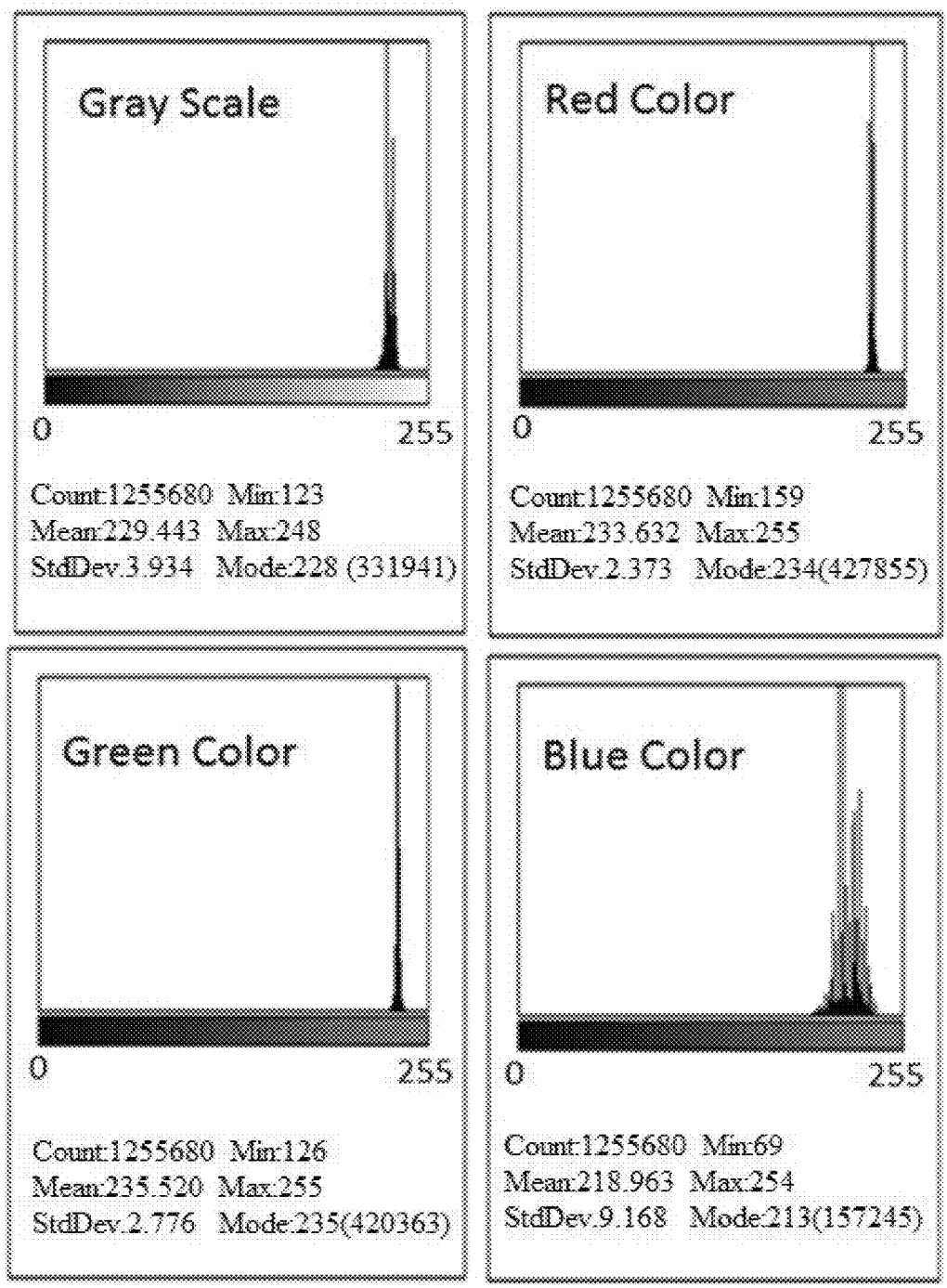
FIGS. 3A-3E are the rendering diagrams of polarizer disposition in accordance with the present invention.

In order to specifically demonstrate the effects of image formation by skin detection device 1 devised with polarizer according to the present invention, the details are concretely described herein. First, if the skin detection device 1 is not provided with any polarizer, the 8 white light LED bulbs will cast directly onto the user's skin (e.g., onto the face of user), and form the reflective light. The reflective light from the user's face is not filtered and enters the lens module 14 directly to form the image, as a result, the user original skin image acquired by the lens module 14 will become too white in the background, and the resolution of the image will be poor. As shown in FIG. 3A, the standard deviations (StdDev) of three primary colors are all too small, and thus the colors and signal-to-noise ratios of three primary colors are not uniformly distributed. In this embodiment, the StdDev of red color is 2.373, the StdDev of green color is 2.776 and the StdDev of blue color 9.618. Furthermore, the excessive grayscale value causes the excessive brightness, which results in a poor resolution of the user original skin image; and it makes the real condition of user's skin cannot be presented appropriately, and hinders the following analysis of user skin condition. However, in this embodiment of the skin detection device 1 according to the present invention, the problems regarding the whitening background and poor resolution of the user original skin image can be just solved.

First, according to an embodiment of the present invention demonstrating the effects of image formation, when the aforementioned second polarizer 13 is disposed at the lateral side of the LED light board 11 facing the skin, the detecting light generated from only 4 of the 8 white light LED bulbs 111, i.e., a half of the detecting light, could pass through the hole 132 to cast onto the skin. Then, when the reflective light projects toward the second polarizer 13, the main part of the reflective light passes through the second polarizer 13, and part of the reflective light becomes scattering light reflected by the skin, and thereby part of light source can be filtered by the second polarizer 13 to weaken the intensity of the light source entering the lens module 14, thereby improving the resolution of the user original skin image. The results of image formation are shown as FIG. 3B. Despite the StdDev of three primary colors are improved, in which the StdDev of red color is 4.830, the StdDev of green color is 7.768 and the StdDev of blue color 12.018. The colors and signal-to-noise ratios of three primary colors are still not uniformly distributed. And the excessive grayscale value still causes the excessive brightness, which results in a poor resolution of the user original skin image; and it makes the real condition of user's skin cannot be presented appropriately, and hinders the following analysis of user skin condition.

Next, in order to solve the abovementioned problems of poor resolution of the user original skin image resulting from the excessive brightness of formed image caused by the excessive grayscale value, (the problem of over-whitening background still unsolved), another preferable embodiment is further provided according to the present invention. In the skin detection device 1, an aforementioned first polarizer 12 is disposed at the lateral side of the LED light board 11 facing the skin, and the detecting light generated from the white light LED bulbs 111 is able to pass the plurality of holes 121 around the first polarizer 12 to cast onto skin. Then, all the reflective light will be first filtered by the first polarizer 12, and the image formation is performed by the lens module 14, and the results of image formation are shown in FIG. 3C, with StdDev of the three primary colors approaching to the median, showing the color and the signal-to-noise ratio of blue and green color of three primary colors become more uniform, while the color and the signal-to-noise ratio of red is still less uniform. In this embodiment, the StdDev of red color is 9.019, the StdDev of green color is 11.014 and the StdDev of blue color 11.208. Apparently, the problem of excessive grayscale value has been improved, and at this time, the skin detection device 1 is able to obtain the original skin image consistent with the real condition of user's skin, and then to perform the following analysis of user's skin condition. However, the problem of over-whitening background still exists in this image.

Furthermore, in order to further improve the aforementioned problem of over-whitening background, another preferable embodiment is provided according to the present invention. In the skin detection device 1, an aforementioned first polarizer 12 and second polarizer 13 are both simultaneously disposed, and the first polarizer 12 and the second polarizer 13 are allocated as shown in FIG. 1B. First, the second polarizer 13 is disposed at the lateral side of the LED light board 11 facing the skin or near the LED lampshade 19, and the first polarizer 12 is disposed between the second polarizer 13 and the LED light board 11, thereby the first polarizer 12 and the second polarizer 13 are overlapped. In a preferable embodiment, when the first polarizer 12 and the second polarizer 13 are disposed to form a rotating angle of polarization of 0 degree (0°) or 180 degree (180°), which means the component materials of these two polarizers are arranged horizontally, at this time, regarding the light reflected from the skin, the main part of the reflective light passes through the hole 131 of the second polarized 13, and further passes through the first polarizer 12, and this first polarizer 12 can filter the scattering light reflected from the skin, and thus filter out the scattering light before casting toward the lens module 14, and the lens module 14 performs the image formation afterward; and the results of image formation are shown in FIG. 3D, with the StdDev of three primary colors approaching to the median, and the color distribution of three primary colors becomes more uniform. In this embodiment, the StdDev of red color is 11.184, the StdDev of green color is 12.717 and the StdDev of blue color 12.413. Apparently, although the noises of three primary colors in FIG. 3D are still obvious, the problem of excessive grayscale value is improved. At this time, the skin detection device 1 is able to obtain the original skin image consistent with the real condition of user's skin, and then to perform the following analysis of user's skin condition.

Figure 3B:
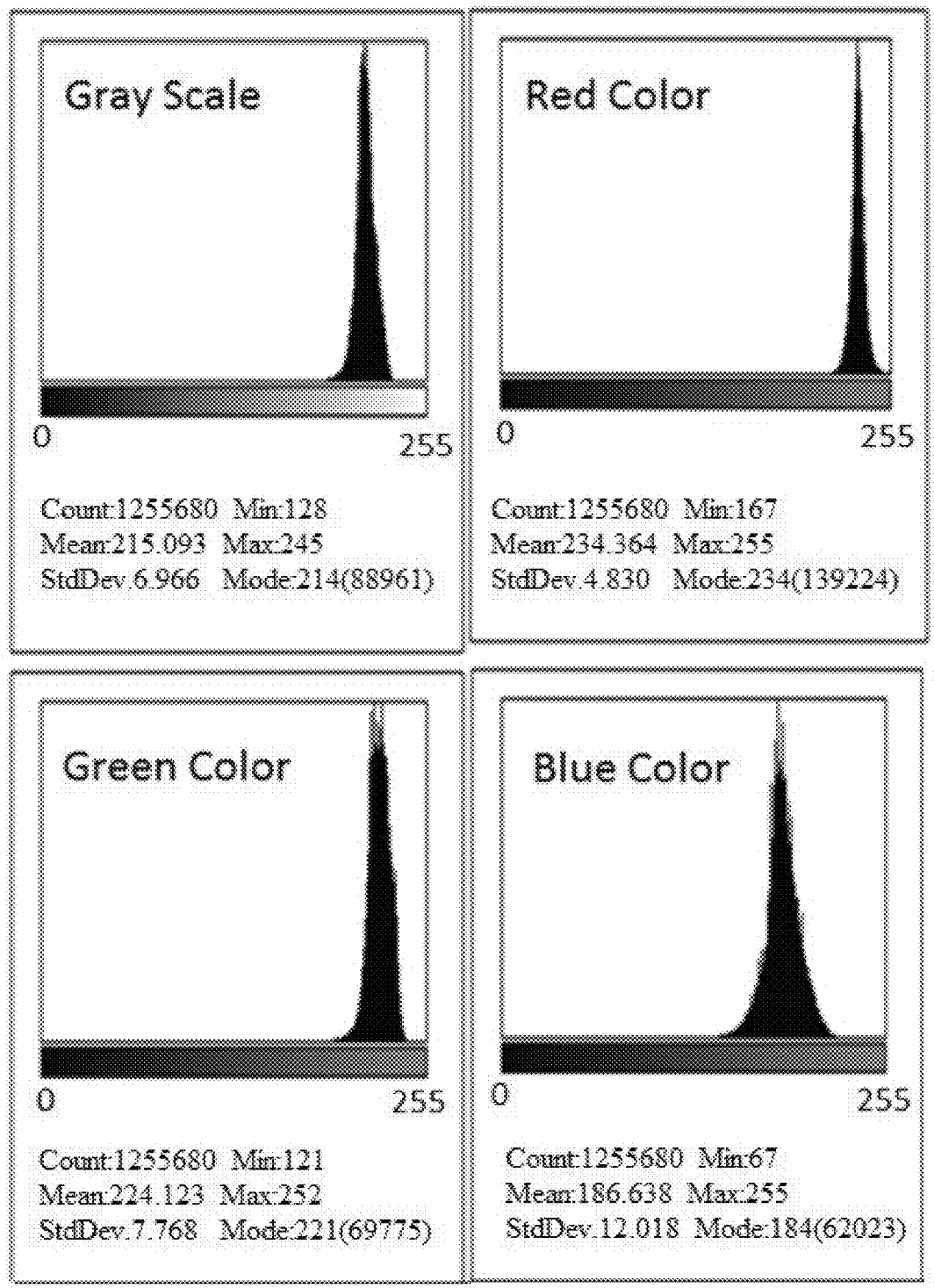
Figure 3C:
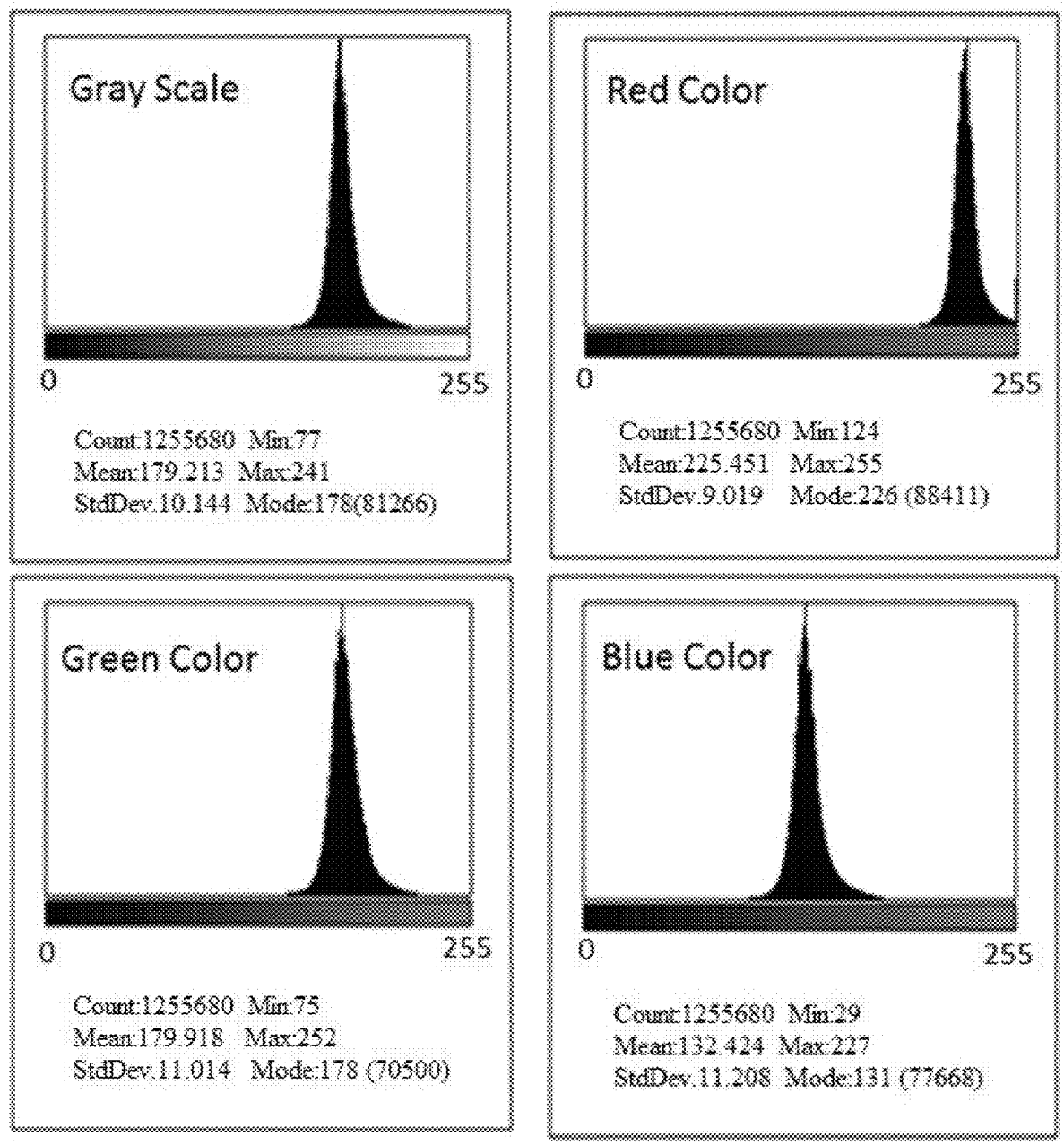
Figure 3D:
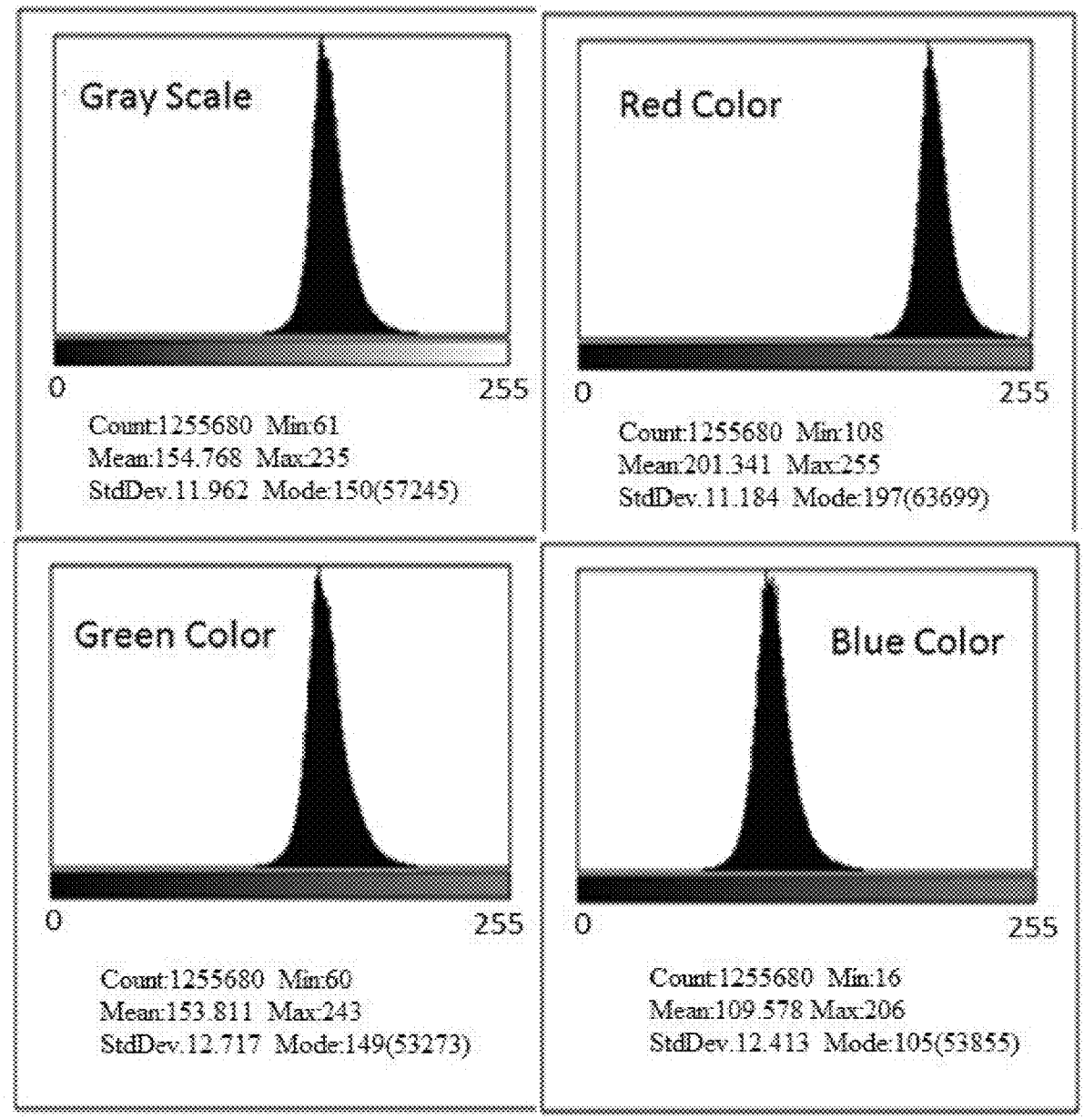
Figure 3E:
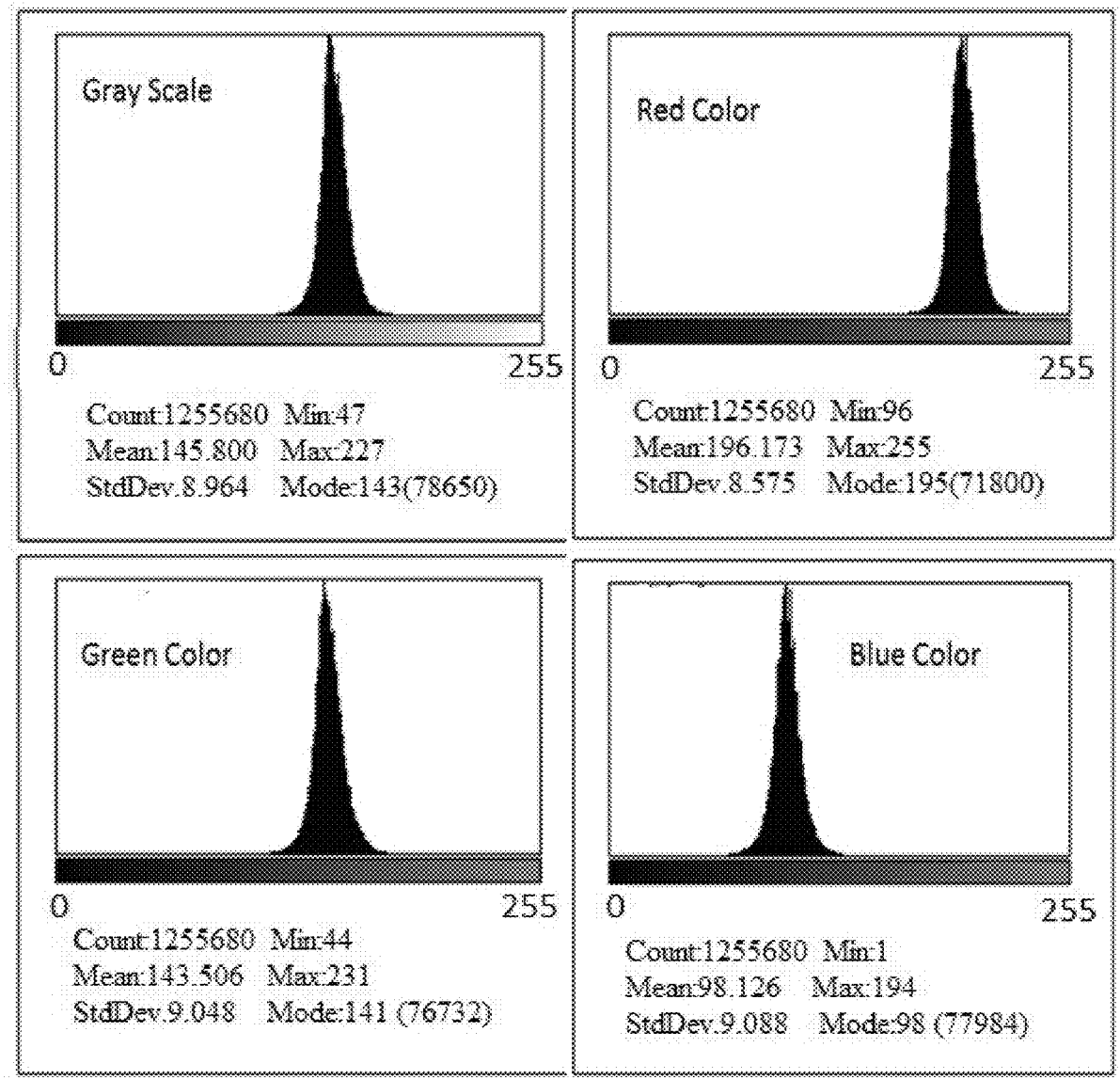

Based on the description of previous paragraph, in a preferable embodiment, when the rotating angle of polarization between the first polarizer 12 and the second polarizer 13 is orthogonal to be 90 degree (90°), which means the component materials of these two polarizers are arranged vertically, at this time, regarding the light reflected from the skin, the main part of the reflective light passes through the hole 131 of the second polarized 13, and further passes through the first polarizer 12, and this first polarizer 12 can filter the scattering light reflected from the skin, and filter out the scattering light before casting toward the lens module 14, and the lens module 14 performs the image formation afterward; and the results of image formation are shown in FIG. 3E, with the StdDev of three primary colors approaching to the median, and the color distributions of blue and green of the three primary colors become more uniform, and the color and signal-to-noise ratio of red is much more uniform than those shown in FIG. 3D. In this embodiment, the StdDev of red color is 8.694, the StdDev of green color is 9.048 and the StdDev of blue color 9.088. Apparently, the problem of excessive grayscale value has been improved. At this time, the skin detection device 1 is able to obtain the original skin image consistent with the real condition of user's skin, and then to perform the following analysis of user's skin condition.

According to the effects on image formation of the obtained user original skin image by allocating the polarizer in the skin detection device 1 according to the present invention, as previously described, it shows that the problem of excessive grayscale value are solved after the skin detection device 1 is disposed at least one first polarizer 12, and therefore the user original skin image obtained by the skin detection device 1 can be used to perform the following analysis of user's skin condition. Particularly, after the first polarizer 12 and the second polarizer 13 are disposed coordinately, regardless of the rotating angle between the first polarizer 12 and the second polarizer 13 is 0° (or 180°), or 90° (orthogonal), the user original skin image obtained by the skin detection device 1 can be used to perform the following analysis of user's skin condition. The effects of polarizer disposition on image formation are now again briefly summarized and tabulated into Table 1 as shown below.

| Polarizer disposition | Effects of image formation |
|---|---|
| No polarizer is disposed. | The color and signal-to-noise ratio are not uniformly distributed; and the grayscale value is excessive which causes the excessive brightness (as shown in FIG. 3A) |
| Only the second polarizer 13 is disposed. | The contrast of the image increases, but the signal-to-noise ratio of each color is still distributed less uniformly; and the excessive grayscale value still results in the over-whitening background (as shown in FIG. 3B) |
| Only the first polarizer 12 is disposed. | The contrast of the image is capable of presenting the real condition of user's skin vividly, while the signal-to-noise ratio of each color is distributed more uniformly; but the red color is oversaturated (as shown in FIG. 3C) |
| The rotating angle between the first polarizer 12 and the second polarizer 13 is 0° or 180°. | The contrast of the image is capable of presenting the real condition of user's skin vividly, while the signal-to-noise ratio of each color is too high (as shown in FIG. 3D) |
| The rotating angle between the first polarizer 12 and the second polarizer 13 is 90°. | The contrast of the image is capable of presenting the real condition of user's skin vividly, and each color and signal-to-noise ratio are distributed uniformly (as shown in FIG. 3E) |

Because the skin detection device according to the present invention provides two kinds of light source, the while light and UV light, thereby this device can obtain two types of information relevant to the user skin condition. One type of the said information is obtained through relevant analysis process to analyze the original image of the user's skin. Based on this original image, the application program installed in the receiving device 2 can process the aforementioned user original skin image, and further obtain various analysis results related to the user's skin condition, such as speckles, textures, pores or wrinkles, and can thereby provide these results to the user and the operator to evaluate the skin condition of the user. In this embodiment, the skin condition includes spot, texture and/or wrinkle. The other type of information is used to determine if there are metal remnants from the cosmetics on the user's skin. If there is remnant metal, such as mercury, on the user skin, the skin lighted by the UV light will illuminate fluorescence, and it thereby indicates that whether the cosmetics used by the user contains metal. Moreover, when the skin is lighted by the UV light, the acne or keratin in the pores can be shown.

Figure 1C:
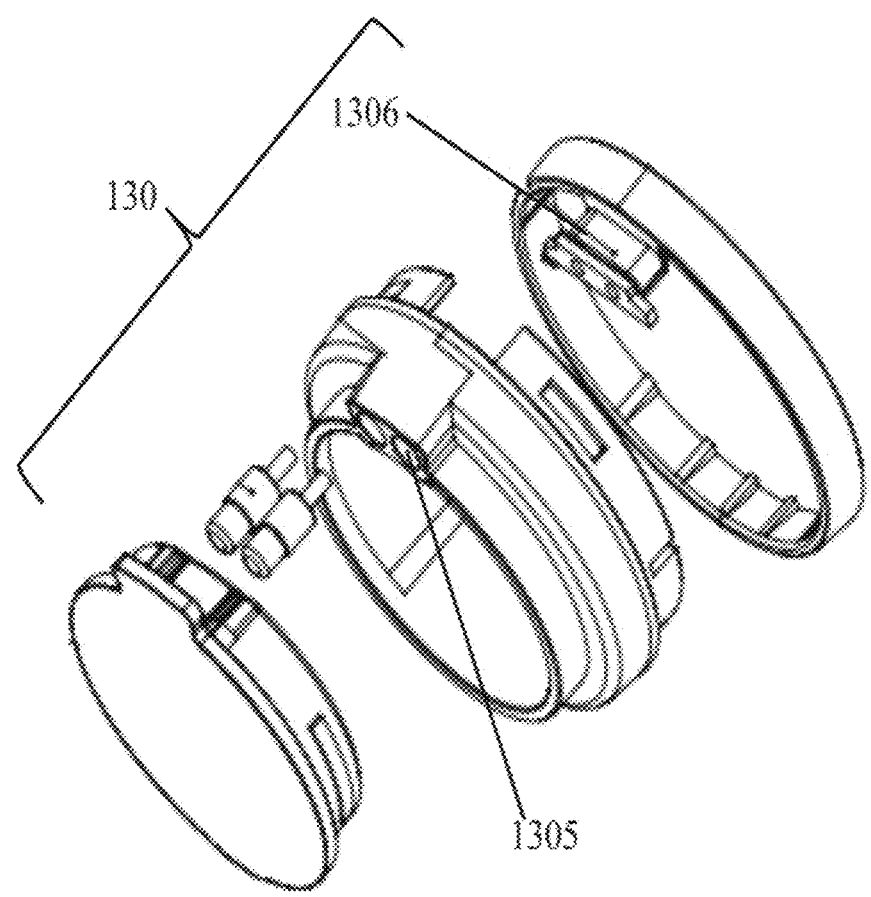
FIG. 1C is an enlarged exploded view of the oil and water detecting portion in the skin detection device in accordance with the present invention.
Figure 2B:
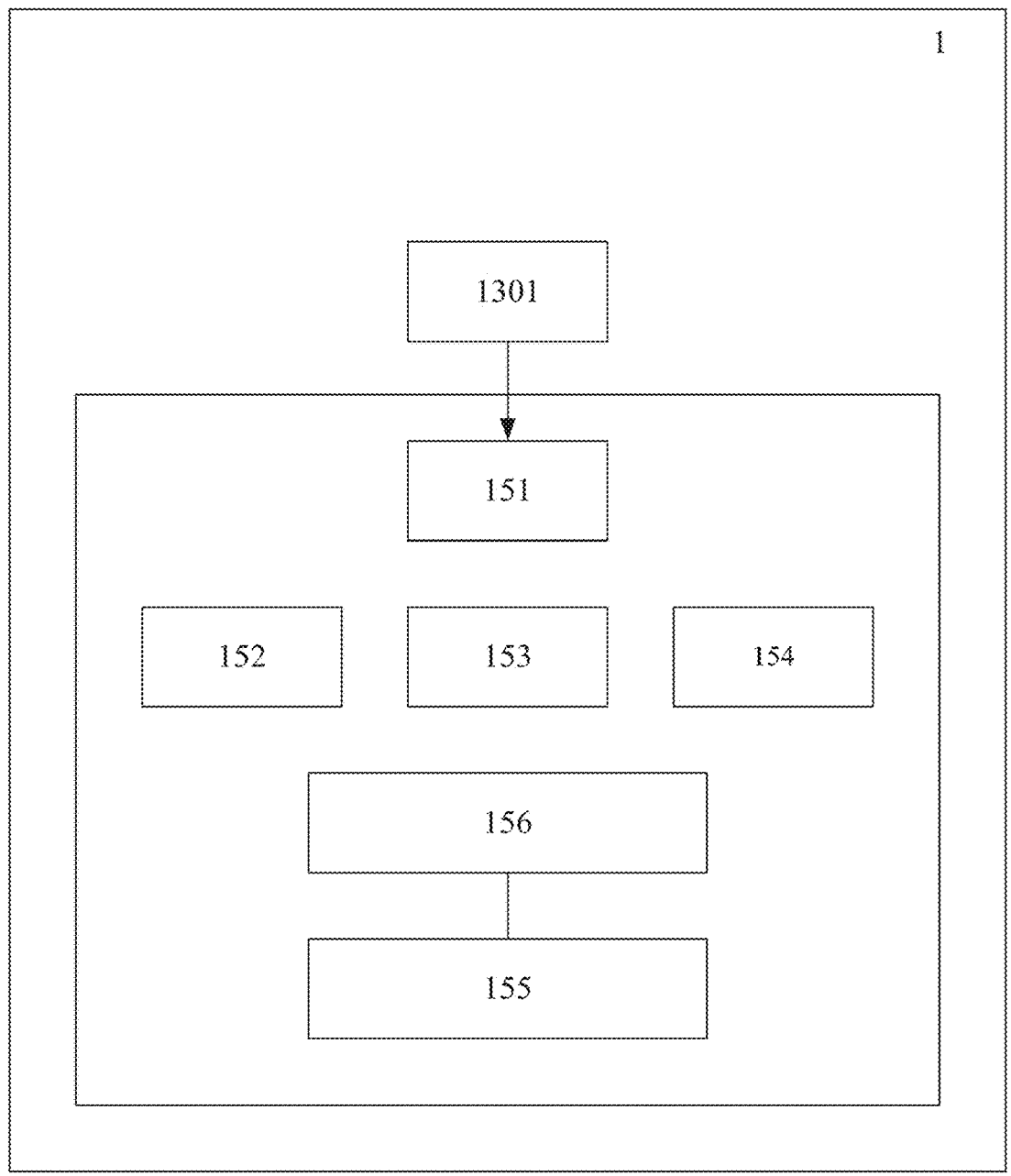
FIG. 2B is a block diagram schematically demonstrating the oil and water detecting portion in the skin detection device in accordance with the present invention.

To enable the skin detection device according to the present invention has the function of determining the oil and water content at the same time, the skin detection device according to the present invention can be further provided with an oil and water detecting component 130. Please refer to FIG. 1C and FIG. 2B to understand the description of practicing the oil and water detecting component 130; wherein FIG. 1C is an enlarged exploded view of the oil and water detecting portion, and FIG. 2B is a block diagram schematically demonstrating the oil and water detecting portion in the skin detection device. First, as shown in FIG. 1C, the oil and water detecting component 130 is devised at the front end (i.e., the end contacting the skin, and the opposite end of tail cover portion 120) of the skin detection device 1, and is connected to the LED lampshade 19. As shown in FIG. 1C, the oil and water detecting component 130 is composed of an oil and water detecting probe 1301, a head cover 1302, a head cover ornamental ring 1303 and a dust cover 1304. The head cover 1302 is provided with a receiving hole 1305, and the receiving hole 1305 is used to fix the oil and water detecting probe 1301 inside the head cover 1302, and thereby the oil and water detecting probe 1301 is connected to a receiving device 1306 configured on the head cover ornamental ring 1303. Besides, a bridging circuit board (not shown in this figure) is provided inside the receiving device 1306, which is used to connect to the connector 151 on the circuit mainboard 15, and it thus allows the user skin oil and water resistance signal acquired by the oil and water detecting probe 1301 to be transmitted to the circuit mainboard 15. Then, the user skin oil and water resistance signal is processed by a signal processing module 156 devised inside the circuit mainboard 15 to obtain the user skin oil and water analyzed frequency. Next, a wireless transmission module 155 transmits this user skin oil and water analyzed frequency to the receiving device 2, as shown in FIG. 2B. And then, the application program installed in the receiving device 2 verifies the abovementioned user skin oil and water analyzed frequency to obtain the analysis result. In this embodiment, the analysis result can show on the display (not shown) of the receiving device 2. Finally, the receiving device 2 presents this analysis result to the user and the operator. In a preferable embodiment, the quantity of the oil and water detecting probe 1301 disposed is two, and the start of the oil and water detecting probe 1301 can also be controlled by the power switch 154 disposed on the circuit mainboard 15. Additionally, the dust cover 1304 can be optionally configured on the head cover 1302, to protect the lens module 14 and the oil and water detecting component 130 in the skin detection device 1, and also to isolate the lens module 14 and the oil and water detecting component 130 from dust for preventing the relevant effects.

Figure 4A:
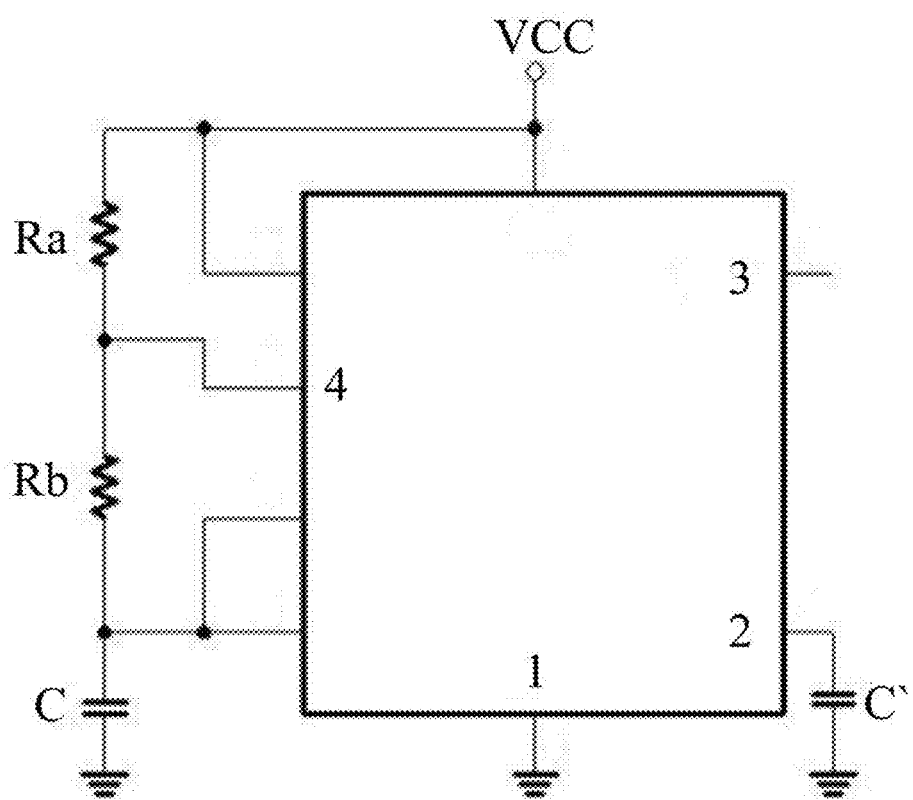
FIG. 4A is a circuit diagram demonstrating the charging and discharging of the user skin oil and water detection in accordance with the present invention.
Figure 4B:
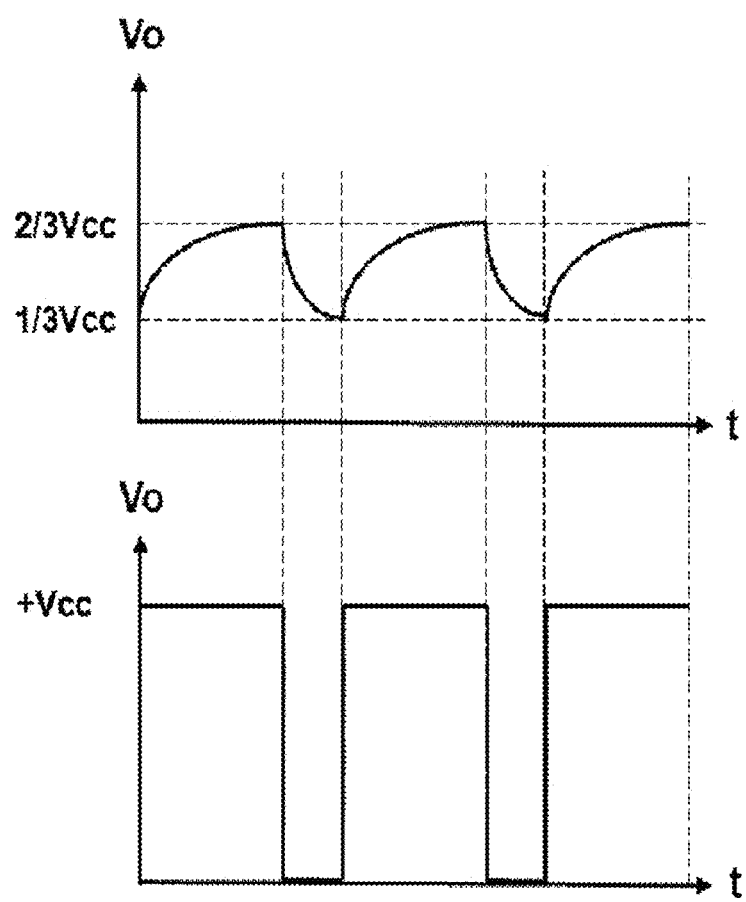
FIG. 4B is a schematic diagram showing the charging and discharging cycle of a capacitor in accordance with the present invention.

To clearly disclose the technical details regarding how the oil and water detecting probe obtains the user skin oil and water analyzed frequency, please read the following description, and meanwhile refer to FIG. 4A and FIG. 4B; wherein FIG. 4A is a circuit diagram demonstrating the charging and discharging of the user skin oil and water detection, and FIG. 4B is a schematic diagram showing the charging and discharging cycle of a capacitor C. First, as shown in FIG. 4A, a pair of parallel sensing resistor (Ra, Rb) and a capacitor C connected to the sensing resistors (Ra, Rb) are disposed on the circuit board inside the receiving device 1306 to form a charging and discharging circuit; wherein this pair of parallel sensing resistor (Ra, Rb) is connected to the oil and water detecting probe 1301 to sense the electrical resistance of user skin with oil and water contents. When the operator operates the skin detection device 1, the pair of parallel sensing resistor (Ra, Rb) can separately sense the electrical resistance of user skin having oil and water content. And the capacitor C and the sensing resistors (Ra, Rb) further form a charging and discharging circuit, wherein the VCC represents the external power source, for example, using a lithium battery as the power source. When the operator uses the oil and water detecting component 130 of the skin detection device 1, and ascertains the electrical resistance generated from the sensing resistors (Ra, Rb), the VCC will charge the capacitor C according to the electrical resistance from the sensing resistors (Ra, Rb).

Next, the operation shown in FIG. 4A is described. When the voltage Vc of the capacitor C is less than one third (⅓) of the voltage of external power source, the output voltage of the flip-flop disposed at the oil and water detecting probe 1301 at the pin 3 is defined as high signal (HI). However, when the voltage Vc of the capacitor C reaches two third (⅔) of the voltage of external power source, the flip-flop is meanwhile reset, and the output voltage of the flip-flop disposed at the oil and water detecting probe 1301 at the pin 3 is defined as low signal (LOW), and thus the capacitor C discharges at the pin 4 through the resistors Rb. While the oil and water detecting probe 1301 detects the oil and water of the user skin, the capacitor C charges and discharges constantly. In this embodiment, a positive and negative device (not shown) is arranged in the pin 3 which is provided for outputting high signal HI) or low signal (LOW). Thereby it obtains a charging and discharging cycle of the capacitor C, as shown in FIG. 4B. In addition, the pin 2 herein further connects to a control capacitor C1 to reduce the interference on the charging and discharging circuit from outside noise. The capacitance of the control capacitor C1 herein is approximately 0.1 uF; and at the same time, the pin 1 lies in grounding and connects to the negative pole of the external power source. As shown in FIG. 4B, the vertical axis Vcc indicates the voltage of external power source, for example, the voltage supplied by lithium battery 16; and meanwhile, because the voltage of external power source is a steady voltage, the charging and discharging cycle of the capacitor C herein is regular, as shown in the lower part of FIG. 4B. T1 represents the time required for charging the capacitor C; T2 represents the time required for discharging the capacitor C; and horizontal axis t indicates the time required for charging and discharging cycle of the capacitor C. When the capacitor C discharges as previously described, the user skin oil and water resistance signal is produced and transmitted to the signal processing module 156 in the circuit mainboard 15 to be processed, wherein the sensing resistors Ra and Rb, and the value of charging and discharging cycle of capacitor C:

$$T1=0.693\times(ra+rb)\times C;\ T2=0.693\times rb\times C,\ \text{and}\ t=T1+T2=1/F$$

Wherein ra represents the resistance of sensing resistors Ra detecting the oil and water content of the user skin; rb represents the resistance of sensing resistors Rb detecting the oil and water content of the user skin; C represents the capacitance of capacitor C; and F represents the charging and discharging frequency. The signal processing module 156 at the circuit mainboard 15 can obtain the charging and discharging frequency F of the capacitor C, which is herein defined as a user skin oil and water analyzed frequency, and is then transmitted by the wireless transmission module 155 to send this user skin oil and water analyzed frequency to the receiving device 2, and the analyzed frequency is then further compared by the application program installed in the receiving device 2, and the comparison basis of the frequency is shown in Table 2. Table 2 is a comparison table of the oil and water analyzed frequency and the user skin oil and water value. By comparing the oil and water analyzed frequency and the user skin oil and water value, the water content and oil content of the user skin are obtained, and these water content and oil content of the user skin can be further used to estimate the softness of user skin. And in a preferable embodiment, the frequency used for user skin oil and water analyzed frequency ranges from 5 KHZ to 120 KHZ. However, the present invention does not limit this range of 5 KHZ to 120 KHZ.

TABLE 2

| | 5 K-30 KHZ | 31 K-80 KHZ | 81 K-120 KHZ |
|---|---|---|---|
| oil and water analyzed frequency | | | |
| value of oil and water | 0-40 | 44-52 | 53-65 |

TABLE 2-continued

| content | | | |
|---|---|---|---|
| water content of user skin | low water content | moderate water content | high water content |
| oil content | high oil content | moderate oil content | low oil content |
| softness | drier skin | moderate skin | softer skin |

Figure 5A:
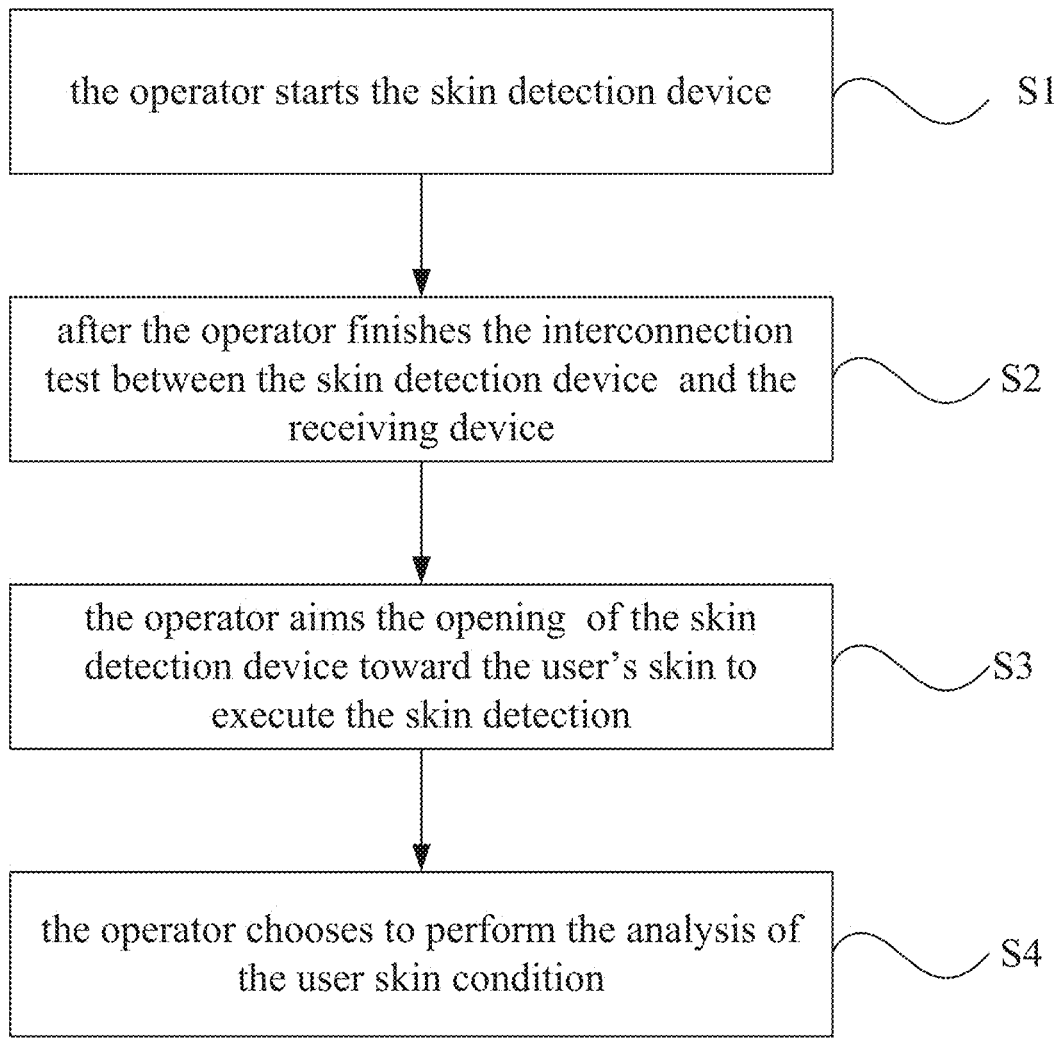
FIG. 5A is a flow chart showing the operation of the skin detection device in accordance with the present invention.

Based on this embodiment, a method of determining user's skin condition using the skin detection device according to the present invention is further provided herein. As shown in FIG. 5A, which is a flow chart showing the operation of the skin detection device. First, as shown by step S1, the operator starts the skin detection device 1, for example, the power switch 154 is pressed to turn on or powers the white light LED bulb 111, lens module 14, and circuit mainboard 15. Next, as shown by step S2, after the operator finishes the interconnection test between the skin detection device 1 and the receiving device 2, it is confirmed that the wireless transmission module devised in the skin detection device 1 and the application program installed in the receiving device 2 are connected. In a preferable embodiment, the application program can be a mobile application suitable for mobile device. Next, as shown by step S3, the operator aims the opening 21 of the skin detection device 1 toward the user's skin (e.g., the face skin) to execute the skin detection, and at the same time, the light source from the white light LED bulb 111 allows the camera unit 141 on the lens module 14 to capture the user skin image and to obtain the polarized light signal which can be further transmitted to the signal processing module 156 to be processed into user original skin image; and then this user original skin image is transmitted to the receiving device 2 via the wireless transmission module 155, and the user's skin is shown on a monitor (not show in this drawing) at the receiving device 2. And next, as shown by step S4, the operator chooses to perform the analysis of the user skin condition, for example, after the user sees her/his skin on the monitor at the receiving device 2 and decides to perform the skin analysis, the operator would press the photography control switch 153 (i.e., shutter button) to take the image, and the skin detection device 1 thus can capture the user original skin image which is further analyzed by an application program installed in the receiving device 2 to obtain an analysis result, and this receiving device 2 can present the analysis result to the user to let the user understand his skin condition according to this method as described in this embodiment. And in a preferable embodiment, the above-mentioned analysis result can be presented as an analysis index to the user.

Figure 5B:
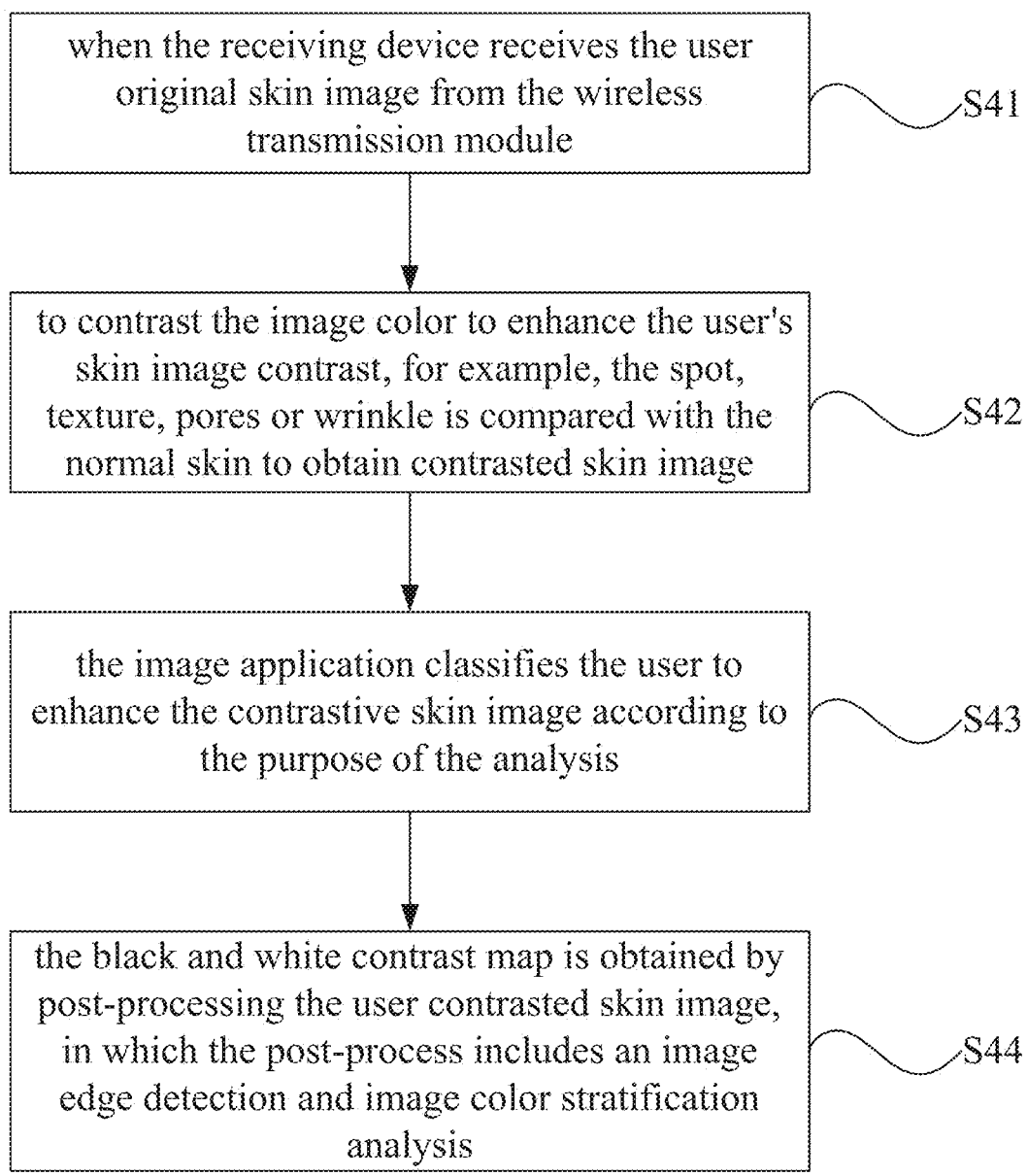
FIG. 5B is a flow chart showing the analysis process of a user original skin image in accordance with the present invention.
Figure 6A:
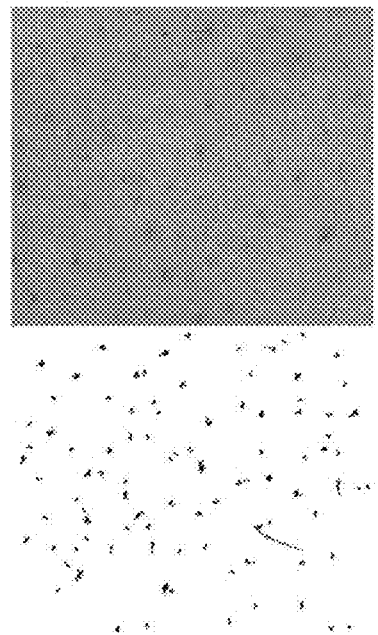
FIG. 6A is a schematic diagram showing the comparison between pores of user skin image in accordance with the present invention.
Figure 6B:
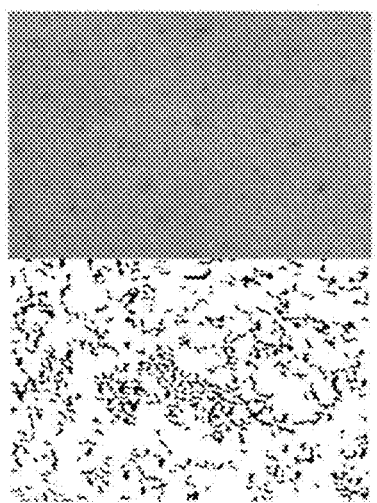
FIG. 6B is a schematic diagram showing the comparison between textures of user skin image in accordance with the present invention.
Figure 6C:
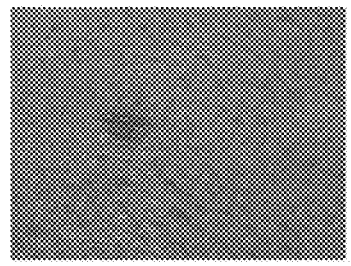
FIG. 6C is a schematic diagram showing the comparison between spots of user skin image in accordance with the present invention.
Figure 6D:
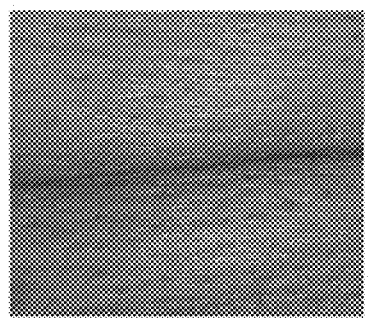
FIG. 6D is a schematic diagram showing the comparison between wrinkles of user skin image in accordance with the present invention.
Figure 6E:
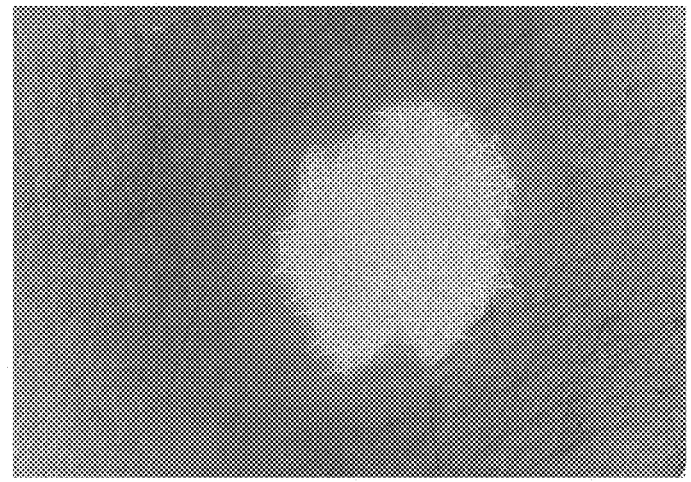
FIG. 6E is a schematic diagram showing the fluorescent response from metals on the skin detected by UV light in accordance with the present invention.
Figure 6F:
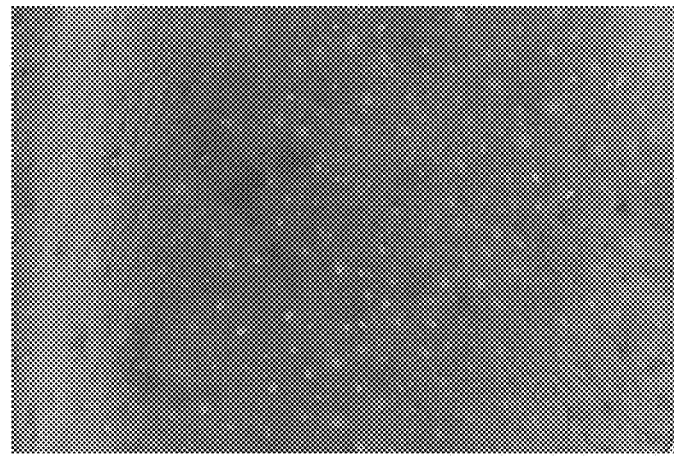
FIG. 6F is a schematic diagram showing the clogged pores and the piling up of keratin on the skin detected by UV light in accordance with the present invention.

Please refer to FIG. 5B, and FIGS. 6A-6F. FIG. 5B is a flow chart showing the analysis process of a user original skin image in accordance with the present invention; FIG. 6A is a schematic diagram showing the comparison between pores of user skin image in accordance with the present invention; FIG. 6B is a schematic diagram showing the comparison between textures of user skin image in accordance with the present invention; FIG. 6C is a schematic diagram showing the comparison between spots of user skin image in accordance with the present invention; FIG. 6D is a schematic diagram showing the comparison between wrinkles of user skin image in accordance with the present invention; FIG. 6E is a schematic diagram showing the fluorescent response from metals on the skin detected by UV light in accordance with the present invention; and FIG. 6F is a schematic diagram showing the clogged pores and the piling up of keratin on the skin detected by UV light in accordance with the present invention. In addition, the top drawing of FIG. 6A to FIG. 6F represents user' skin image after analysis process and the bottom drawing of FIG. 6A to FIG. 6F represents the black and white comparison chart of the user's skin image, in which the black region which is reinforced by contrast represents the skin spot, texture, wrinkle or pores that are contrast and the white region represents the normal skin region.

First, step S41: when the receiving device 2 receives the user original skin image from the wireless transmission module 155, the image is pre-processed by an image application of the receiving device 2, in which the pre-process includes image size cutting and image back noise removal, etc, and the user's skin image can be obtained such that the user's skin image can facilitate the subsequent analysis steps. Step S42: to contrast the image color to enhance the user's skin image contrast, for example, the spot, texture, pores or wrinkle is compared with the normal skin to obtain contrasted skin image. Step S43: the image application classifies the user to enhance the contrastive skin image according to the purpose of the analysis. The purpose of the above analysis includes the skin defects and the skin texture. In one embodiment of the present invention, the skin defect includes spot and pores. The skin testure includes wrinkle and texture. Step S44: the black and white contrast map is obtained by post-processing the user contrasted skin image, in which the post-process includes an image edge detection and image color stratification analysis. The algorithm for image edge detection can be a canny algorithm and the algorithm for image color hierarchical analysis can be a Fuzzy Cooth algorithm, it is not to limit in the present invention.

The image application can further calculate the percentage of black region in the black and white comparison chart, and the percentage of the statistics is analyzed by analyzing the index and presented by the receiving device 2 to the user and the operator. For example, when the image application is provided for analyzing the size of the skin pores, the percentage of the black region is 20% in the comparison chart obtained after the above analysis procedure, the receiving device 2 will present the analysis result of the pore analysis index 20 to the user and the operator. Also, the skin detection device 1 can obtain the above skin condition by using image application and the analysis result of skin condition is used as a basis to provide the beauty recommendations for users.

Obviously, as shown in top of FIG. 6A, the skin detection device 1 can analysis accurately the size and position of pores within the user's skin. Then, the bottom of FIG. 6A represents the size clearly. As shown in top of FIG. 6B, the skin detection device of the present invention can analysis the size and the position of skin texture image. The bottom of FIG. 6B represents the image of size and the position of skin texture within the user's skin clearly. As shown in top of FIG. 6C, the skin detection device 1 can analysis accurately the image of size and position of spot within the user's skin. The bottom of FIG. 6C represents the size and position of spot within the user's skin clearly. As shown in FIG. 6D, the skin detection device 1 can accurately analysis the image of size and the position of wrinkle. The bottom of FIG. 6D represents the size and position of wrinkle within the user's skin. In addition, as shown in FIG. 6E, the metal fluorescence reaction the on the skin can be showed obviously when the skin detection device 1 is irradiated with a specific wavelength of UV light. Accordingly, the skin detection device 1 can provide for detecting whether the metal component on the user's skin. As shown in FIG. 6F, the skin detection device of the present invention can utilize the different color to represent the acne and breeding bacteria within the user's skin when the skin detection device 1 is irradiated with a specific wavelength of UV light, so that the skin detection device 1 can provide for detecting the cleanliness of the skin pores.

To allow the skin detection device provided by the present invention to provide the user with the analysis result of his/her skin condition, wherein this analysis result is presented as an analysis index and thereby letting the user and operator to know the user skin condition, an analysis process and the method thereof are further provided herein. Please refer to FIG. 5B and FIGS. 6A to 6D when reading the following description, wherein FIG. 5B is a flow chart showing the analysis process of a user original skin image, and FIGS. 6A to 6D are schematic diagrams showing the comparison of user skin image obtained via analysis process, those which include the user skin image preprocessed (upper panel) and the user skin image shown in black-and-white contrast diagram (lower panel), wherein the black area in the black-and-white contrast diagram represents the spots, texture, size or wrinkles area acquired after contrast intensification; and the white areas is normal skin area. First, as shown by step S41, after the receiving device 2 receives a user original skin image transmitted from wireless transmission module 155, the application program installed in the receiving device 2 will preprocesses the image, such as adjusting the image size, removing the background noise of the image and so on, to help the following analysis steps. Next, as shown by step S42, the contrast of the user skin image is enhanced by image color enhancing contrast, such as intensifying the contrast between the spots, texture, pores or wrinkles and the normal skin in the image, and thereby obtaining the contrast-enhanced user skin image. And next, as shown by step S43, according to different purposes of analysis, the image application program will sort the abovementioned contrast-enhanced user skin image. The aforesaid purposes of analysis include skin defects and skin textures; and in an embodiment, the skin defects include spots and pores, while the skin textures include wrinkles and lines. The following analysis is performed based on the sorting result. And next, as shown by step S44, the contrast-enhanced user skin image is post-processed to obtain the black-and-white contrast diagram as previously described, as shown in FIGS. 6A to 6D. The post-process includes an image edge detection and an image color stratification analysis, wherein the algorithm used for the image edge detection can be practiced by Canny algorithm, and the algorithm used for the image color stratification analysis can be practiced by Fuzzy C means algorithm, those which are not limited in this embodiment. The application program herein can further calculate the percentage of the black area in the black-and-white contrast diagram, and this calculated percentage is presented as an analysis index to the user and operator by the receiving device 2. For example, when the application program analyzes the pore size of the user skin and a contrast diagram is obtained by abovementioned analysis process, if the percentage of the black area calculated is 20%, the receiving device 2 will present the analysis result as a pore size analysis index of 20 to the user and operator. Based on the same rationale, the skin detection device can obtain various information relevant to the user skin condition, such as the pore size, dullness of spots, the severity of wrinkles, and thus it provides the user with the basis for following aesthetical advices.

To allow the skin detection device provided by the present invention to determine the oil and water content of user skin, to further obtain the softness of user skin, an analysis process regarding the user skin oil and water content and the method thereof are further provided herein. Please refer to FIG. 5C and read the following description, wherein FIG. 5C is a flow chart showing the analysis process of a user skin oil and water content. First, the user skin oil and water resistance signal is obtained by the oil and water detecting probe 1301 configured in the skin detection device, and the user skin oil and water resistance signal is then transmitted to the circuit mainboard 15 for being processed into a user skin oil and water analyzed frequency, which is transmitted to the receiving device 2 by the wireless transmission module 155 for being compared. In a preferable embodiment, this user skin oil and water analyzed frequency ranges from 5 KHz-120 KHz. Next, as shown by step S45, an application program installed in the receiving device 2 performs the comparison of the user skin oil and water analyzed frequency, and thus the water content and the oil content of user skin is obtained correspondingly, and the oil and water content of user skin is further used to analyze the softness of the user skin. In a preferable embodiment, if the user oil and water analyzed frequency received is 8 KHz, the application program will verify that the value of oil and water content of user skin to be 25, and thereby determine the water content of user skin is 25%. And the oil content of user skin is categorized as highly oily, and the softness of user skin at that time is characterized to be highly oily. If the user oil and water analyzed frequency received is 120 KHz, the application program will verify that the value of oil and water content of user skin to be 65, and thereby determine the water content of user skin is 65%. And the oil content of user skin is categorized as less oily, and the softness of user skin at that time is characterized to be less oily. Finally, as shown by step S46, the receiving device 2 presents the previously described analysis results on the oil and water content of user skin and the softness of user skin to the user and operator, and thus it provides the user with the basis for the following aesthetical advices.

In view of the previous description, the analysis process disclosed in the present invention can be used for analyzing the user original skin image and the user skin oil and water analyzed frequency obtained by the skin detection device, and thereby determining complete indexes of the user skin condition, such as pore size, dullness of spots, severity of wrinkles, water content, oil content and softness; and in another embodiment, the application program can be installed inside the skin detection device 1, and the wireless transmission module 155 can transmit the result analyzed by the application program to the receiving device 2, and ultimately the analyzed result is presented by the receiving device 2.

The receiving device 2 herein can be further used for networking the cloud database to establish an individualized database of the user to follow up the user's skin condition. For example, when it is found that there are problems of enlarged pore size or too oily skin, these detection results can be recorded in the individualized database, and then be kept following the user's skin condition, and the individualized database can be updated at all times, therefore, the improvement of skin condition is followed and thereby the efficiency of the cosmetic consultation can be improved.

The above is only description of exemplary preferable embodiments of the present invention, and is not intended to limit the scope of the present invention. Meanwhile, the above description should be apparent and practicable to those skilled in the art, therefore various equivalent changes and alterations may be made therein without departing from the essence of the invention, and it is intended to cover herein all such changes and alterations as coming within the true scope of the annexed claims.

What is claimed is:

1. A skin detection device, comprising:

a light-emitting diode light board equipped with a plurality of white light light-emitting diode bulbs and a plurality of ultraviolet light-emitting diode bulbs, for providing the skin detection device with a detecting light required for operation, the light-emitting diode light board is provided with a hollow area configured in the middle, the plurality of white light light-emitting diode bulbs and ultraviolet light-emitting diode bulbs are arranged to encircle the hollow area of the light-emitting diode light board to form a concentric circle, wherein the white light light-emitting diode bulbs are arranged at the periphery of the concentric circle, and the ultraviolet light-emitting diode bulbs are arranged at an intermediate circle of the concentric circle;

a lampshade configured to be at front ends of an upper cover and a lower cover for supporting connection between the upper cover and the lower cover, and configured to form an opening contacting with a skin of a user;

a first polarizer formed into a flat plate and configured on the light-emitting diode light board, comprising a plurality of first holes corresponding to a number of the white light light-emitting diode bulbs at a rim of the first polarizer in order to allow the detecting light generated to pass through the plurality of first holes in the first polarizer and to cast onto the skin of the user;

a second polarizer disposed at a side of the light-emitting diode light board facing the skin, and overlapped at the first polarizer disposed between the second polarizer and the light-emitting diode light board, wherein a central hole is provided in a center of the second polarizer corresponding to the hollow area of the light-emitting diode light board, and a plurality of second holes is provided between the central hole and a rim of the second polarizer corresponding to the number of the white light light-emitting diode bulbs, the plurality of second holes is used for shading the detecting light generated by the white light light-emitting diode bulbs, the main part of the reflected light passes through the central hole of the second polarizer, and further passes through the first polarizer, wherein a reflective scattering light reflected from the skin is filtered out by the first polarizer before casting toward a lens module to obtain a polarized light signal;

the lens module with one end connected to an end of the light-emitting diode light board, the lens module includes a flexible board and a camera unit penetrating the hollow area of the light-emitting diode light board, the camera unit comprises a complementary metal oxide semiconductor image sensor for receiving the polarized light signal and then converting the polarized light signal into an electrical signal;

a circuit mainboard with an end provided with a connector connected to an end of the flexible board of the lens module for transmitting the electrical signal to the circuit mainboard, wherein the circuit mainboard is configured with a light source control switch, a photography control switch, a power switch, a wireless transmission module, and a signal processing module, and the signal processing module of the circuit mainboard is used for receiving and processing the electrical signal into a user original skin image;

the lower cover having an accommodating space, wherein the accommodating space contains the light-emitting diode light board, the lens module, the circuit mainboard, and a charging board; and the upper cover provided with a plurality of buttons connected with the light source control switch, the photography control switch, and the power switch; and an oil and water detecting portion, connected to the lampshade, the oil and water detecting portion comprising an oil and water detecting probe connected with the circuit mainboard to allow a user skin oil and water resistance signal acquired by the oil and water detecting probe to be transmitted to the signal processing module of the circuit mainboard, then the wireless transmission module transmits the user original skin image and/or the user skin oil and water resistance signal to a receiving device.

2. The skin detection device according to claim 1 further comprising a charging board with one end connected to the other end of the circuit mainboard, wherein the charging board is used for charging.

3. The skin detection device according to claim 1, wherein a charging and discharging circuit is devised inside the oil and water detecting portion.

4. The skin detection device according to claim 1, further comprising a tail cover portion configured near the rear ends of the upper cover and the lower cover, wherein the tail cover portion comprises a tail cover ornamental ring, a tail cover and a tail cover soft plug; the tail cover soft plug is configured on the tail cover; and one end of the tail cover is connected to the tail cover ornamental ring.

5. The skin detection device according to claim 1, wherein the receiving device is a tablet or a smart phone.

6. The skin detection device according to claim 1, wherein the second polarizer is disposed between the first polarizer and the lateral side of the light-emitting diode light board facing the skin, wherein the first polarizer and the second polarizer are thereby overlapped.

7. The skin detection device according to claim 6, wherein the rotating angle of polarization between the first polarizer and the second polarizer is adjustable to produce various polarization effects of image formation.

* * * * *